(12) United States Patent
Vacca

(10) Patent No.: US 9,658,148 B2
(45) Date of Patent: May 23, 2017

(54) PARTICLE ANALYSIS AND SORTING APPARATUS AND METHODS

(71) Applicant: Kinetic River Corp., Cupertino, CA (US)

(72) Inventor: Giacomo Vacca, Campbell, CA (US)

(73) Assignee: Kinetic River Corp., Mountain View, CA (US)

( * ) Notice: Subject to any disclaimer, the term of this patent is extended or adjusted under 35 U.S.C. 154(b) by 46 days.

(21) Appl. No.: 14/879,079

(22) Filed: Oct. 8, 2015

(65) Prior Publication Data
US 2016/0103056 A1    Apr. 14, 2016

Related U.S. Application Data

(60) Provisional application No. 62/062,133, filed on Oct. 9, 2014.

(51) Int. Cl.
*G01N 15/14* (2006.01)
*G01N 15/10* (2006.01)

(52) U.S. Cl.
CPC ........... *G01N 15/14* (2013.01); *G01N 15/147* (2013.01); *G01N 15/1429* (2013.01);
(Continued)

(58) Field of Classification Search
CPC .............. G01N 15/14; G01N 15/1429; G01N 15/1434; G01N 15/147; G01N 2015/1006;
(Continued)

(56) References Cited

U.S. PATENT DOCUMENTS

| 5,224,058 | A | 6/1993 | Mickaels et al. |
| 5,317,612 | A | 5/1994 | Bryan et al. |

(Continued)

FOREIGN PATENT DOCUMENTS

WO    2009052467 A1    4/2009

OTHER PUBLICATIONS

Cui et al., "Fluorescence Lifetime-Based Discrimination and Quantification of Cellular DNA and RNA With Phase-Sensitive Flow Cytometry", Cytometry Part A, vol. 52A, 2003, pp. 46-55.
(Continued)

*Primary Examiner* — Mark R Gaworecki
(74) *Attorney, Agent, or Firm* — Aurora Consulting LLC; Wouter Roorda; Ashley Sloat

(57) ABSTRACT

A particle analyzer, comprising a source of a beam of pulsed optical energy; a detector comprising a number of spectral detection channels to detect optical signals resulting from interactions between the beam and particles in a sample (such as, e.g., fluorescence signals), and to convert the optical signals into respective electrical signals; optical paths from the source to the sample and from the sample to the detector; a flowcell connected with the optical paths and with a flow path for a suspension of particles; a signal processing module capable of: receiving the electrical signals from the detector; mathematically combining individual decay curves in the signals into a decay supercurve; allocating individual components of the supercurve to discrete bins of predetermined time constants; and quantifying the relative contribution of individual components to the supercurve; a particle sorting actuator; an actuator driver; and at least one particle collection receptacle.

18 Claims, 20 Drawing Sheets

(52) U.S. Cl.
CPC . *G01N 15/1434* (2013.01); *G01N 2015/1006* (2013.01); *G01N 2015/149* (2013.01); *G01N 2015/1477* (2013.01); *G01N 2015/1488* (2013.01)

(58) Field of Classification Search
CPC ... G01N 2015/1477; G01N 2015/1488; G01N 2015/149
See application file for complete search history.

(56) References Cited

U.S. PATENT DOCUMENTS

| | | |
|---|---|---|
| 5,504,337 A | 4/1996 | Lakowicz et al. |
| 5,909,278 A | 6/1999 | Deka et al. |
| 7,890,157 B2 | 2/2011 | Jo et al. |
| 2006/0062698 A1 | 3/2006 | Foster et al. |
| 2008/0292555 A1 | 11/2008 | Ye et al. |

OTHER PUBLICATIONS

Houston, et al., "Capture of Fluorescence Decay Times by Flow Cytometry", Current Protocols in Cytometry, Unit 1.25, 2012, 21 pgs.

International Search Report mailed Jan. 6, 2016 from International Application No. PCT/US2015/054948, 2 pgs.

Steinkamp, John A. "Fluorescence Lifetime Flow Cytometry", Emerging Tools for Single-Cell Analysis; Advances in Optical Measurement Technologies, 2000, pp. 175-196.

Steinkamp, John A. "Time-Resolved Fluorescence Measurements", Current Protocols in Cytometry, Unit 1.15, 2000, 16 pgs.

Li, et al., "Fluorescence lifetime excitation cytometry by kinetic dithering", Electrophoresis, vol. 00, 2014, pp. 1-9.

Written Opinion of International Search Report mailed Jan. 6, 2016 from International Application No. PCT/US2015/054948, 7 pgs.

Yu et al., "Fluorescence Lifetime Imaging: New Microscopy Technologies", Emerging Tools for Single-Cell Analysis: Advances in Optical Measurement Technologies, 2000, pp. 139-173.

PARTICLE ANALYSIS AND SORTING APPARATUS AND METHODS

INTRODUCTION

The invention pertains to the fields of Particle Analysis and Particle Sorting. In particular, embodiments of the invention are capable of increased multiplexing in Flow Cytometry and Cell Sorting.

BACKGROUND

Cellular analysis and sorting have reached a high level of sophistication, enabling their widespread use in life science research and medical diagnostics alike. Yet for all their remarkable success as technologies, much remains to be done in order to meet significant needs in terms of applications.

One area of continuing unmet need is that of multiplexing. Multiplexing refers to the practice of labeling cells, beads, or other particles with multiple types of biochemical or biophysical "tags" simultaneously and detecting those tags uniquely, so as to generate a richer set of information with each analysis. The most commonly used tags in microscopy and flow cytometry are fluorescent molecules, or fluorophores. A fluorophore may be a naturally occurring fluorophore; it may be an added reagent; it may be a fluorescent protein [like, e.g., Green Fluorescence Protein (GFP)] expressed by genetic manipulation; it may be a byproduct of chemical or biochemical reactions, etc. Fluorophores may be used as they are, relying on their native affinity for certain subcellular structures such as, e.g., DNA or RNA; or they may be linked to the highly specific biochemical entities known as antibodies, in a process referred to as conjugation. As a particular antibody binds to a matching antigen, often on the surface of a cell, the fluorophore conjugated to that antibody becomes a "tag" for that cell. The presence or absence of the fluorophore (and therefore of the antigen the fluorophore-conjugated antibody is intended to specifically bind to) can then be established by excitation of the cells in the sample by optical means and the detection (if present) of the fluorescence emission from the fluorophore. Fluorescence emission into a certain range of the optical spectrum, or band, is sometimes referred to in the art as a "color;" the ability to perform multiplexed analysis is therefore sometimes ranked by the number of simultaneous colors available for detection.

The use of multiple distinct tags (and detection of their associated colors) simultaneously allows the characterization of each cell to a much greater degree of detail than possible with the use of a single tag. In immunology particularly, cells are classified based on their expression of surface antigens. The identification of a large number of different surface antigens on various types of cells has motivated the creation of a rich taxonomy of cell types. To uniquely identify the exact type of cell under analysis, it is therefore often necessary to perform cell analysis protocols involving simultaneously a large number of distinct antibody-conjugated tags, each specifically designed to identify the presence of a particular type of antigen on the cell surface.

In flow cytometry of the prior art, methods have been devised to simultaneously label cells with up to twenty or more different fluorescent tags and detect their respective colors. Commercially available instrumentation is generally limited to simultaneous detection of fifteen colors or less, and most commonly less than about ten colors. One of the main challenges of routinely performing highly multiplexed analysis (as the practice of simultaneously detecting more than about a dozen separate colors is sometimes called) is the technical difficulty of keeping detection of each color (and its associated tag) separate from detection of all the other ones. FIG. 1 illustrates one key aspect of the challenge of multiplexed measurement of fluorescence in the prior art. The graph in this FIG. 1 depicts various fluorescence emission curves (thin solid lines) of intensity (I) as a function of wavelength ($\lambda$), all curves having been normalized to their respective peak intensities. In applications of fluorescence detection, it is very commonly desirable to employ several different colors, or spectral bands, of the electromagnetic spectrum, and to assign each band to a different fluorophore. Different fluorophores can be selected, on the basis of their average emission spectra, so as to obtain relatively dense coverage of a certain range of the electromagnetic spectrum, and thereby maximize the amount of information that can be extracted in the course of a single experiment or analysis "run." However, when striving to maximize spectral coverage, one of the common undesirable consequences is spectral overlap. The shaded portions in FIG. 1 illustrate the problem caused by spectral overlap between adjacent fluorescence spectra. In this particular illustrative example, five spectral fluorescence "bands" or colors (the five emission curves peaking at different wavelengths) span a certain desired range of the electromagnetic spectrum, such as, e.g., the visible portion of the spectrum from about 400 nm to about 750 nm in wavelength. The shaded portions indicate sections of the spectrum where it is impossible, using spectral means alone, to decide whether the signal comes from one or the other of the two bands adjacent to the overlapping region; accordingly, the portions of the spectrum corresponding to significant overlap are commonly discarded, resulting in inefficient use of the spectrum. Additionally, even after discarding such portions, residual overlap remains in the other portions, resulting in contamination of one band from signals from other bands. Attempts at negating the deleterious effects of such contamination go under the heading of "compensation." This spectral overlap problem is variously described in the literature and the community as the "crosstalk," the "spillover," the "compensation problem," etc., and it is a major factor in limiting the maximum number of concurrent spectral bands, or colors, that can be employed in a fluorescence detection experiment.

It would be desirable, then, to provide a way to perform highly multiplexed analyses of particles or cells with a reduced or eliminated impact of spectral crosstalk.

In cell analysis of the prior art, methods have also been devised to simultaneously label cells with up to thirty of more different tags and detect their respective characteristics. For example, the technique known in the art as mass cytometry employs not fluorescence as a way to distinguish different tags, but mass spectrometry, where the tags incorporate not fluorophores, but different isotopes of rare earths identifiable by their mass spectra. One major drawback of this approach is that the protocol of analysis is destructive to the sample, the cells and their tags becoming elementally vaporized in the process of generating the mass spectra. This approach is therefore not suited to the selection and sorting of cells or other particles following their identification by analysis.

It would be further desirable, then, to provide a way to perform selection and sorting of particles or cells based on nondestructive highly multiplexed analysis with a reduced or eliminated impact of spectral crosstalk.

SUMMARY

An apparatus for analyzing an optical signal decay, comprising:
a source of a beam of pulsed optical energy;
a sample holder configured to expose a sample to said beam;
a detector, the detector comprising a number of spectral detection channels, said channels being sensitive to distinct wavelength sections of the electromagnetic spectrum and being configured to detect optical signals resulting from interactions between said beam and said sample, said channels being further configured to convert said optical signals into respective electrical signals;
a first optical path from said source of said beam to said sample;
a second optical path from said sample to said detector; and
a signal processing module, capable of:
receiving said electrical signals from said detector;
mathematically combining individual decay curves in said electrical signals into a decay supercurve, said supercurve comprising a number of components, each component having a time constant and a relative contribution to said supercurve;
extracting time constants from said supercurve; and
quantifying the relative contribution of individual components to said supercurve.

An apparatus for analyzing an optical signal decay, comprising:
a source of a beam of pulsed optical energy, wherein said source of said beam of pulsed optical energy is an internally modulated laser;
a flowcell configured as an optical excitation chamber for exposing to said beam a sample comprising a suspension of particles and for generating optical signals from interactions between said beam and said particles;
a detector, the detector comprising a number of spectral detection channels, said channels being sensitive to distinct wavelength sections of the electromagnetic spectrum and being configured to detect said optical signals, said channels being further configured to convert said optical signals into respective electrical signals, wherein said optical signals comprise a fluorescence signal;
a first optical path from said source of said beam to said sample, said first optical path being connected with said flowcell;
a second optical path from said sample to said detector, said second optical path being connected with said flowcell;
a signal processing module, wherein said signal processing module comprises one of an FPGA, a DSP chip, an ASIC, a CPU, a microprocessor, a microcontroller, a single-board computer, a standalone computer, and a cloud-based processor, said signal processing module being further capable of:
receiving said electrical signals from said detector;
mathematically combining individual decay curves in said electrical signals into a decay supercurve, said supercurve comprising a number of components, each component having a time constant and a relative contribution to said supercurve;
extracting time constants from said supercurve; and
quantifying the relative contribution of individual components to said supercurve;
a flow cytometer;
a flow path for said suspension of particles, said flow path being connected with said flowcell;
a particle sorting actuator connected with said flow path, wherein said particle sorting actuator is based on at least one flow diversion in said flow path, and wherein said particle sorting actuator is further based on one of a transient bubble, a pressurizable chamber, a pressurizable/depressurizable chamber pair, and a pressure transducer;
an actuator driver connected with said actuator, said driver being configured to receive actuation signals from said signal processing module; and
at least one particle collection receptacle connected with said flow path.

An apparatus for analyzing an optical signal decay, comprising:
a source of a beam of pulsed optical energy;
a sample holder configured to expose a sample to said beam;
a detector, the detector comprising a number of spectral detection channels, said channels being sensitive to distinct wavelength sections of the electromagnetic spectrum and being configured to detect optical signals resulting from interactions between said beam and said sample, said channels being further configured to convert said optical signals into respective electrical signals;
a first optical path from said source of said beam to said sample;
a second optical path from said sample to said detector; and
a signal processing module, capable of:
receiving said electrical signals from said detector;
mathematically combining individual decay curves in said electrical signals into a decay supercurve, said supercurve comprising a number of components, each component having a time constant and a relative contribution to said supercurve;
allocating individual components of said supercurve to discrete bins of predetermined time constants; and
quantifying the relative contribution of individual components to said supercurve.

An apparatus for analyzing an optical signal decay, comprising:
a source of a beam of pulsed optical energy, wherein said source of said beam of pulsed optical energy is an internally modulated laser;
a flowcell configured as an optical excitation chamber for exposing to said beam a sample comprising a suspension of particles and for generating optical signals from interactions between said beam and said particles;
a detector, the detector comprising a number of spectral detection channels, said channels being sensitive to distinct wavelength sections of the electromagnetic spectrum and being configured to detect said optical signals, said channels being further configured to convert said optical signals into respective electrical signals, wherein said optical signals comprise a fluorescence signal;
a first optical path from said source of said beam to said sample, said first optical path being connected with said flowcell;
a second optical path from said sample to said detector, said second optical path being connected with said flowcell;

a signal processing module, wherein said signal processing module comprises one of an FPGA, a DSP chip, an ASIC, a CPU, a microprocessor, a microcontroller, a single-board computer, a standalone computer, and a cloud-based processor, said signal processing module being further capable of:

receiving said electrical signals from said detector;

mathematically combining individual decay curves in said electrical signals into a decay supercurve, said supercurve comprising a number of components, each component having a time constant and a relative contribution to said supercurve;

allocating individual components of said supercurve to discrete bins of predetermined time constants; and quantifying the relative contribution of individual components to said supercurve;

a flow cytometer;

a flow path for said suspension of particles, said flow path being connected with said flowcell;

a particle sorting actuator connected with said flow path, wherein said particle sorting actuator is based on at least one flow diversion in said flow path, and wherein said particle sorting actuator is further based on one of a transient bubble, a pressurizable chamber, a pressurizable/depressurizable chamber pair, and a pressure transducer;

an actuator driver connected with said actuator, said driver being configured to receive actuation signals from said signal processing module; and at least one particle collection receptacle connected with said flow path.

DETAILED DESCRIPTION

One possible solution to the spectral overlap problem in highly multiplexed particle and cell analysis would be to utilize, beside spectral information, another type of information with which to index or encode the tags used to label cell characteristics. By adding an independent quantity that can be detected and measured, one can significantly increase the number of combinations available to label and identify cell types. There would follow then a reduced need to fit a large number of independent spectral bands into a limited region of the electromagnetic spectrum, since the total number of available combinations could be allocated based on two independent quantities instead of just one.

It is one objective of the present invention to provide fluorescence lifetime as that independent quantity, to be combined with spectral labeling to generate a highly multiplexed set of independent combinations with which to uniquely tag different cell characteristics or cell types with a reduced or eliminated impact of spectral crosstalk.

It is a further objective of the present invention to provide the combination of fluorescence lifetime and spectral fluorescence labeling to aid not only in the highly multiplexed analysis of cells or other particles, but also in the selection and sorting of cells or other particles with a reduced or eliminated impact of spectral crosstalk.

Fluorescence lifetime is an aspect of the fluorescence emission process governed by quantum-mechanical laws. Fluorescence is the absorption by an atom or molecule of a packet of optical energy (a photon) of a certain wavelength and the subsequent emission by the same atom or molecule of a packet of optical energy (another photon) at a longer wavelength. The amount of time elapsed between absorption and emission varies stochastically, but given an ensemble of isolated identical atoms or molecules, the frequency distribution of such elapsed times of the entire ensemble follows an exponential decay curve. The time constant of such a curve (the 1/e time) is referred to as the lifetime for that fluorescence transition for that atom or molecule.

Figure 1:
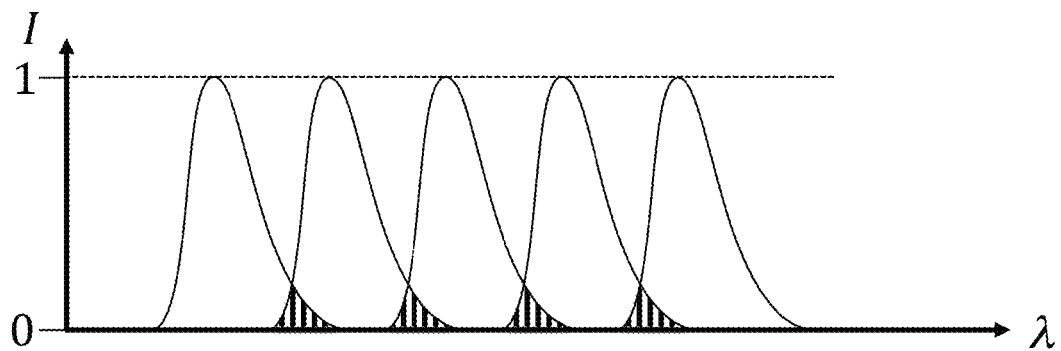
FIG. 1 is a wavelength diagram illustrating the spectral overlap (spillover) in multiplexing approaches of the prior art.

Different molecular entities display different fluorescence transitions, characterized by different optimal wavelengths of optical absorption, different peak wavelengths of optical emission, and different fluorescence lifetimes. Certain molecular entities display fluorescence transitions with similar spectral characteristics (the profiles of emission as a function of wavelength schematically illustrated in FIG. 1) but with different fluorescence lifetimes. And other molecular entities display fluorescence transitions with different spectral characteristics but with similar fluorescence lifetimes. Accordingly, molecular entities may be selected based on spectral characteristics (spectral emission profile) and fluorescence lifetime as essentially independent quantities.

Figure 2:
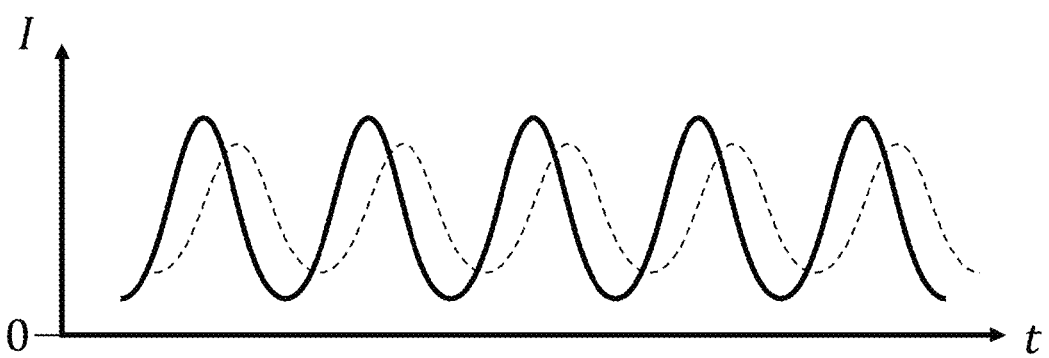
FIG. 2 is a time-domain diagram illustrating a frequency-based approach to measuring single-exponential fluorescence lifetime of the prior art.

In order to use fluorescence lifetime as a multiplexing parameter in particle analysis, one needs to provide the means to measure it. FIG. 2 describes one aspect of measurements of fluorescence lifetime as carried out in one approach in the prior art. The graph in this FIG. 2 depicts two curves of optical intensity (I) as a function of time (t). In this approach, the intensity of optical excitation (thick solid line) is modulated at a certain frequency, and the resulting fluorescence signal (thin dashed line) is analyzed. The effect of a finite fluorescence lifetime manifests itself primarily in the phase shift between the modulated excitation and the modulated emission curves. The main drawback of this approach (so-called "phase-sensitive" or "frequency-domain" fluorescence lifetime) is that it can only probe one fluorescence lifetime component at a time, and is poorly suited to analysis of samples where more than one lifetime component should be measured simultaneously. It is an objective of the current invention to overcome this limitation.

Figure 3:
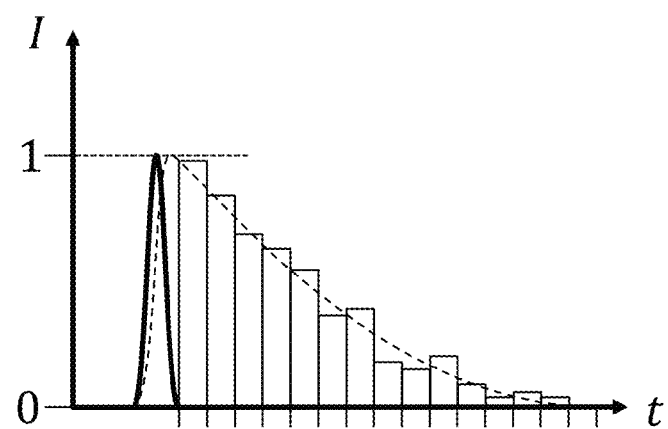
FIG. 3 is a time-domain diagram illustrating a time-correlated single-photon counting approach to measuring fluorescence lifetime of the prior art.

FIG. 3 illustrates the principle behind another approach to measurement of fluorescence lifetime in the prior art. This approach has been referred to in the literature as Time-Correlated Single-Photon Counting (TCSPC), and has been used particularly in fluorescence lifetime imaging applications (FLIM). The graph depicted in this FIG. 3 shows two curves of intensity (I) as a function of time (t), both normalized to unit peak intensity, and a histogram with associated bins. The first curve (thick solid line) represents any one of many identical excitation pulses used to interrogate a portion of the sample; the second curve (thin dashed line) represents the inferred fluorescence emission response from the portion of the sample under interrogation. This second curve is not measured directly, but is instead inferred by a numerical fit to a histogram. A typical hypothetical histogram is shown as a series of boxes superimposed upon the second curve. This histogram represents the frequency distribution of arrival times of single fluorescence emission photons following excitation by a pulse. By exciting the same portion of the sample many times, a histogram is collected that faithfully reflects the underlying fluorescence decay curve. The main drawback of this approach is the very principle it is based on: single-photon counting. The method only works if a single photon is, on average, emitted as a result of excitation. For typical decay curves, it is not uncommon to require between tens of thousands and millions of repeated excitations in order to acquire enough statistics in the histogram for acceptable accuracy of results. Even at high pulse repetition rates, this approach necessarily results in dwell times (the time spent acquiring data on a single portion of the sample) on the order of milliseconds to seconds. Accordingly, TCSPC is an approach that has been successfully applied to stationary samples, but which is poorly suited to samples that are rapidly varying, unstable, flowing, or generally needing to be analyzed rapidly. It is an objective of the current invention to overcome this limitation.

Figure 4:
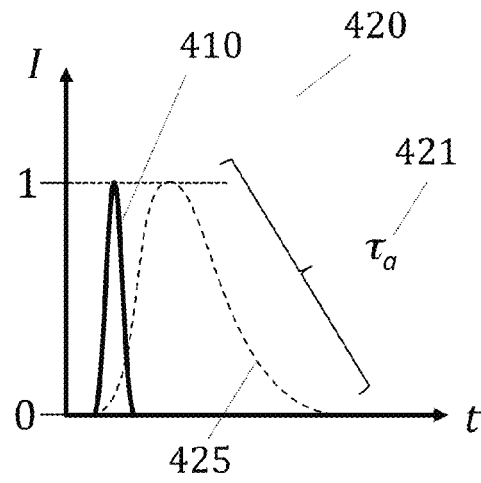
FIG. 4(a) is a linear-linear time-domain diagram and FIG. 4(b) is a log-linear time-domain diagram illustrating a single-exponential decay curve resulting from pulsed excitation.
FIG. 4(c) is a linear-linear time-domain diagram and FIG. 4(d) is a log-linear time-domain diagram illustrating a double-exponential decay curve resulting from pulsed excitation.
Figure 4:
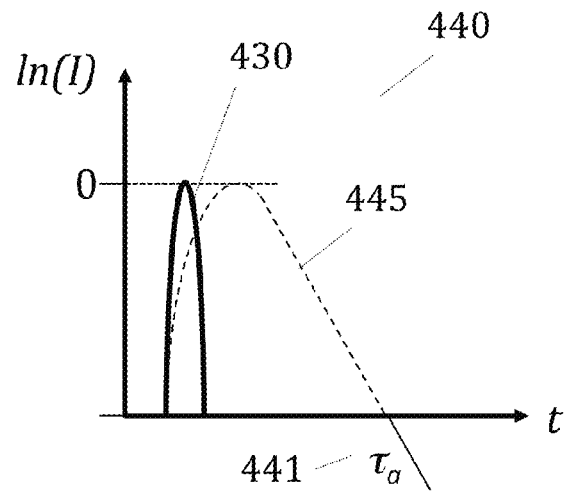
Figure 4:
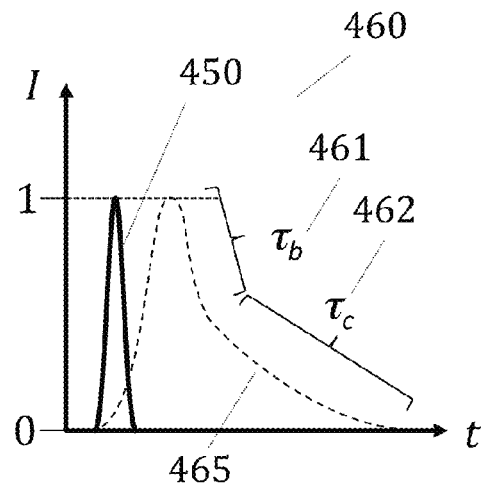
Figure 4:
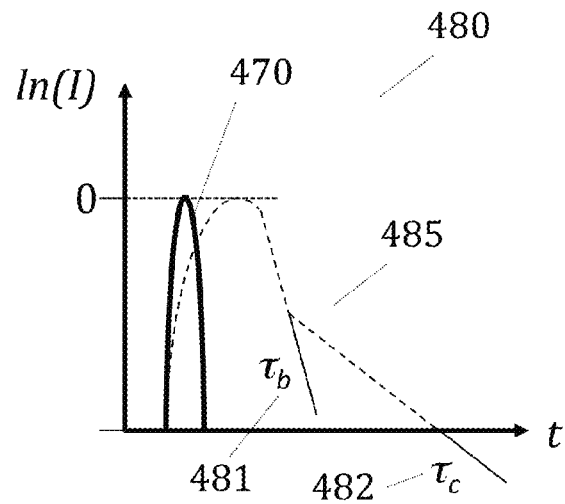

FIGS. 4(a)-(d) illustrate the importance of direct time-domain measurements of fluorescence lifetime. In each of FIGS. 4(a)-(d), a graph depicts the evolution in time (t) of the intensity (I) of two curves: the optical excitation pulse (shown as thick solid lines 410, 430, 450, and 470, in the four graphs, respectively) and the optical emission curve (shown as thin dashed lines 425, 445, 465, and 485, in the four graphs, respectively), both being normalized to unit peak intensity. In FIGS. 4(a) and 4(c), each of the two curves in each graph 420 and 460 are plotted on a linear-linear scale; in FIGS. 4(b) and 4(d), each of the two curves in each graph 440 and 480 are plotted on a log-linear scale (also known as a "semilog" scale). The graphs 420 and 440 in FIGS. 4(a) and 4(b) illustrate the same curves, just plotted on different scales; likewise, the graphs 460 and 480 in FIGS. 4(c) and 4(d) illustrate the same curves, just plotted on different scales. In fluorescence processes, a molecule (which can be naturally occurring, such as certain dyes; or manmade, such as the majority of fluorophores in current use) exhibits a propensity for absorption of optical energy within a certain range of wavelengths (referred to as its absorption spectrum), followed by emission of optical energy into a different range of wavelengths (referred to as its emission spectrum). The process of absorption and emission in fluorescence is governed by quantum mechanics and is influenced by several factors. Some of those factors are intrinsic to the molecule; other factors are environmental factors. Emission of a fluorescent photon occurs stochastically; given a large enough collection of identical molecules (an ensemble), the collective emission of the ensemble will appear to decay over time. For a homogeneous ensemble [depicted in FIGS. 4(a) and 4(b)], the cumulative curve of fluorescence emission can be represented by a single decay lifetime (shown schematically as $\tau_a$ 421 in this case). In the semilog plot 440 of FIG. 4(b), the single-decay nature of the dashed emission curve 445 is evidenced by the presence of a single straight slope (indicated by its corresponding lifetime $\tau_a$ 441, corresponding to the same $\tau_a$ as 421 in plot 420). For a heterogeneous ensemble [depicted in FIGS. 4(c) and 4(d)] consisting of two distinct populations, the cumulative curve of fluorescence emission can be better represented by a compound function comprising two different decay lifetimes (shown schematically as $\tau_b$ 461 and $\tau_c$ 462 in this case). In the semilog plot 480 of FIG. 4(d), the double-decay nature of the dashed emission curve 485 is evidenced by the presence of two straight-sloped branches (indicated by their respective lifetimes $\tau_b$ 481 and $\tau_c$ 482, respectively corresponding to $\tau_b$ 461 and $\tau_c$. 462 in plot 460) joined at a "knee." The shape of the decay curve gives information regarding the environment of the molecules in the ensemble. Assuming that the ensemble in FIGS. 4(c) and 4(d) consisted of a single kind of molecular entity, the appearance of two distinct lifetimes would suggest that molecules in the ensemble are exposed to two different environmental influences, one of them causing a significant alteration to the native fluorescence lifetime of the molecules. Without a direct recording in real time of the actual shape of the emission decay curve of the ensemble of fluorescence molecules, the distinction between the cases depicted in FIGS. 4(a)-(b) and FIGS. 4(c)-(d) would be lost, and with it the information regarding the environment of the molecular species. The analysis made possible by this direct time-domain approach can be variously referred to as multi-component or multi-exponential fluorescence decay analysis.

A practical example of application of the principle of analysis of multi-exponential, or multi-component, fluorescence decay is found in the analysis of cells. A eukaryotic cell consists primarily of a membrane, a cytoplasm, a nucleus, and various subcellular cytoplasmic structures. The biochemical microenvironment experienced by a molecule within a cell is greatly affected by factors such as the local concentration of electrolytes, local pH, local temperature, etc. When a fluorophore enters a cell, its microenvironment may be very different, depending on whether the fluorophore is freely floating in the cytoplasm, binds to a molecule (e.g., RNA) or to an enzyme or other subcellular structures within the cytoplasm, or crosses the nuclear membrane to bind to, e.g., DNA in the nucleus. When exposed to optical excitation, the sub-ensemble of fluorophores bound to DNA in the nucleus may exhibit a very different lifetime from, e.g., the sub-ensemble of fluorophores freely floating in the cytoplasm. By analyzing the compound decay curve of the entire ensemble, one must be able to distinguish between the two (or more) different contributions to the lifetime, as an average single lifetime will blur the desired information and present an incomplete picture of the situation.

If the cell to be analyzed is stationary (as, e.g., adhered to a substrate, or grown on a substrate, suitable for placement under a microscope), existing microscopy tools could be used to spatially resolve physical locations within the cell, perform, e.g., highly repetitious experiments on single pixels (or voxels) spanning very small portions of the cell, and repeat these measurements over all pixels (or voxels) comprising the cell. There are however, many instances when that approach is not desirable, and it would be instead advantageous for the cell to be analyzed to be moving swiftly past the point of interrogation. One instance is when it is desirable to complete a set of measurements on a cell or on a group of cells in a very short time, as is generally the case in clinical diagnostic applications, where time-to-results is a critical parameter on which may depend patients' health or lives. A related instance, also of great relevance in clinical diagnostics and drug discovery and development, but increasingly also recognized as important in basic scientific research, is when it is desirable to complete a certain set of measurements on a very large collection of cells in a practical amount of time, so as to generate statistically relevant results not skewed by the impact of individual outliers. Another instance is when it is desirable to perform measurements on a cell in an environment that mimics to the greatest degree possible the environment of the cell in its native physiological state: As an example, for cells naturally suspended in flowing liquids, such as all blood cells, adhesion to a substrate is a very unnatural state that grossly interferes with their native configuration. There are yet instances where the details of the physical location within the cell (details afforded, at a price of both time and money, by high-resolution microscopy) are simply not important, but where a proxy for specific locations within the cell would suffice, given prior knowledge (based on prior offline studies or results from the literature) about the correlation between specific cell locations and values of the proxy measurement.

There are also instances where, regardless of the speed at which a measurement is carried out, and therefore regardless of whether the measurement is performed on a flow cytometer, under a microscope, or under some other yet experimental conditions, it would be desirable to reduce or eliminate the spectral crossover problem. Many analytical protocols in cell biology research, drug discovery, immunology research, and clinical diagnostics are predicated on the concurrent use of multiple fluorophores, in order to elucidate various properties of highly heterogeneous samples consisting of diverse cell populations, sometimes with uncertain origin or lineage. The spectral crossover inherent in such concurrent use of available fluorophores presently limits the multiplexing abilities of tools in current use—be they cell sorters, cell analyzers, image-based confocal scanning microscopes, or other platform. Various schemes have been developed to quantify and mitigate the deleterious impact of spectral crossover, and are generally referred to as compensation correction schemes. These schemes, however, suffer from overcomplexity, lack of reproducibility, and difficulty in the proper training of operators. It would be therefore advantageous to provide various analytical platforms with a way to multiplex complex measurements without the same attendant spectral crossover issue as is currently experienced.

There are yet instances of cellular analysis where it is desirable to perform fluorescence lifetime measurements on molecular species native to the systems under study. In this case the process of fluorescence is sometime referred to as autofluorescence or endogenous fluorescence, and it does not depend on the introduction of external fluorophores, but rather relies on the intrinsic fluorescence of molecules already present (generally naturally so) in the cell to be analyzed. Endogenous fluorescence is similar to the fluorescence of externally introduced fluorophores, in being subject to similar effects, such as the influence of the molecular microenvironment on fluorescence lifetime. Accordingly, it would be advantageous to be able to resolve different states of endogenous fluorescence on an analytical platform, so as to provide for simple and direct differentiation between cells belonging to different populations known to correlate with different values of endogenous fluorescence lifetime of one or more natively present compounds. One example of practical application of the principle of endogenous fluorescence is in the differential identification of cancer cells from normal cells based on metabolic information.

Figure 5:
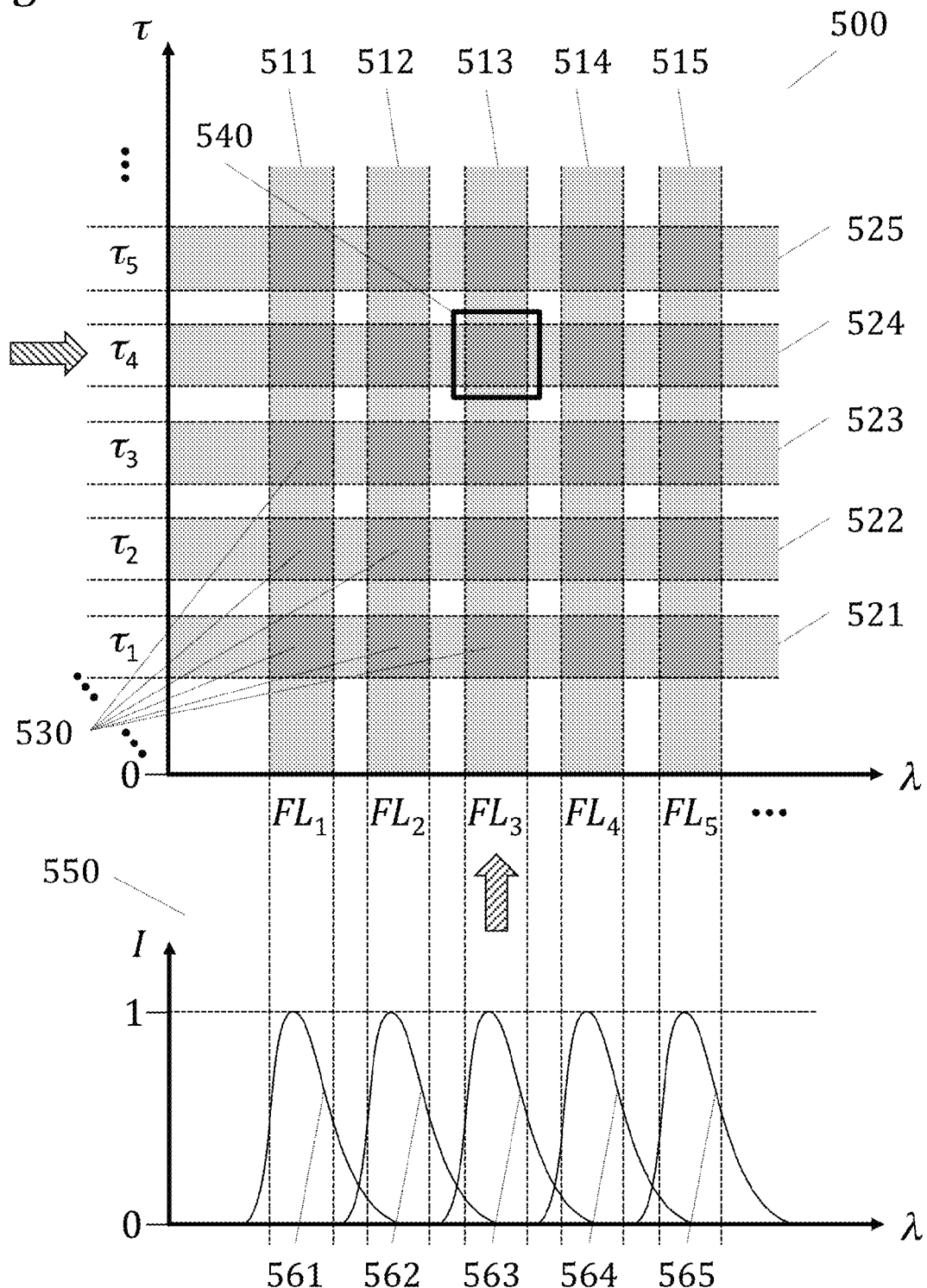
FIG. 5 is a wavelength-lifetime diagram coupled with a wavelength diagram illustrating a multiplexing approach dense in both spectral bands and lifetime bins in accordance with one embodiment.

FIG. 5 schematically illustrates a principle of the present invention, namely the ability to improve the multiplexing capacity of an analytical instrument by using fluorescence lifetime information. At the bottom of FIG. 5 is a graph 550 depicting various fluorescence emission curves 561-565 (thin solid lines) of intensity (I) as a function of wavelength (λ), all curves having been normalized to their respective unit peak intensity. In contrast to the prior art, where distinction between different fluorophores as cell labels or "markers" is performed exclusively by spectral means (the horizontal wavelength axis λ in graph 550), in the present invention a separate, orthogonal dimension of analysis is added: the vertical lifetime τ axis in the graph 500 at top. Each fluorescence emission curve is represented by a "band", shown in the figure as a shaded vertical strip 511-515: $FL_1$ (511), $FL_2$ (512), $FL_3$ (513), $FL_4$ (514), $FL_5$ (515), . . . . Similarly, different fluorescence lifetime values are represented by different values of τ, grouped together in "bins", shown in the figure as shaded horizontal strips 521-525: $\tau_1$ (521), $\tau_2$ (522), $\tau_3$ (523), $\tau_4$ (524), $\tau_5$ (525), . . . . Each of the bins is intended to schematically represent a relatively similar group of lifetimes: the variation among the various lifetime values in the $\tau_1$ bin will generally be smaller than the difference between the average lifetimes of the $\tau_1$ and $\tau_2$ bins, the variation among the various lifetime values in the $\tau_2$ bin will generally be smaller than the difference between the average lifetimes of the $\tau_1$ and $\tau_2$ bins and will also generally be smaller than the difference between the average lifetimes of the $\tau_2$ and $\tau_3$ bins, and so on.

FIG. 5 makes it plain that the wavelength axis and its associated bands now represent only one dimension of a virtual plane. The second, added dimension of this virtual plane is represented by the fluorescence lifetime axis τ and its associated bins in graph 500. The schematic intersections of the wavelength bands and the lifetime bins are shown in graph 500 as darker shaded regions 530 (of which only a few are labeled) in the λ-τ plane. The increased multiplexing of the present invention is exemplified by the fact that, for every one of the spectral (wavelength) bands generally available to current analytical platforms, the present invention offers several possible multiplexed lifetimes: As an example, the fluorescence band $FL_2$ (512) supports multiple fluorescence lifetime bins $\tau_1$ (521), $\tau_2$ (522), $\tau^3$ (523), $\tau_4$ (524), $\tau_5$ (525), . . . . For a system with n distinct fluorescence bands and m distinct lifetime bins, the total theoretical number of independent combinations is n×m; to use a practical example, for a system with 6 distinct fluorescence bands and 4 distinct lifetime bins, there are 6×4=24 mutually independent multiplexed combinations available.

FIG. 5 also describes how a specific example of a multiplexed combination would be resolved in the present invention. From the wavelength axis a particular spectral band (say, $FL_3$ band 513) is selected for analysis. This particular spectral band in practice would be selected by spectral optical means, such as one or more of thin-film filters, dichroic beam splitters, colored glass filters, diffraction gratings, and holographic gratings, or any other spectrally dispersing means suitable for the task and designed to pass this band of wavelengths preferentially over all others. The resulting optical signal could still comprise any of a number of fluorescence lifetimes, depending on the instrument design and on the nature of the sample. The spectral optical signal filtered through as $FL_3$ is detected, converted to electronic form, and sent to an electronic signal processing unit for digitization and further elaboration; see FIG. 10. The signal processing unit (further described below in reference to FIGS. 7 and 19) performs an analysis of the decay characteristics of the optical signals corresponding to the particle under study, and allocates the various contributions to the overall signal from each possible band of lifetime values. A virtual electronic "bin" corresponding to the specific bin $\tau_4$ (524) of lifetimes would receive a value corresponding to the fraction of the signal that could be ascribed as resulting from a lifetime decay within the acceptable range relevant for the $\tau_4$ band. The combination of the spectral filtering for $FL_3$ performed optically on the emitted signal and the lifetime filtering for $\tau_4$ performed digitally on the electronically converted optical signal results in narrowing down analysis to a single multiplexing element: the shaded intersection 540 marked with a thick solid square in graph 500 of FIG. 5.

The specific choice of $FL_3$ and $\tau_4$ is only illustrative, in the sense that any of the intersections between detectable spectral fluorescence bands and resolvable lifetime bins are potentially simultaneously accessible by analysis—resulting in the increased multiplexing ability described above as desirable. FIG. 5 shows explicitly a set of allowable multiplexed intersections for a prophetic example comprising 5 distinct fluorescence bands and 5 distinct lifetime bins: a resulting set of up to 5×5=25 separate, mutually independent combinations. This example is illustrative only: the number of possible combinations is not limited to 25, being given instead by the number of individually separable fluorescence spectral bands multiplied by the number of individually separable lifetime values bins. The theoretical maximum number of individually separable lifetime bins is related to the sampling frequency of digitization, the repetition rate of excitation pulses, and the duration (width) of each excitation pulse. In the limit of excitation pulses much shorter than lifetimes of interest (which are typically in the tens of picoseconds to tens of nanoseconds, and which in some cases reach microsecond levels or greater), the maximum number of separable lifetime bins is given by the pulse repetition period divided by twice the digitization sampling period. Electronic, optical, and other noise effects in actual systems may significantly reduce this theoretical maximum.

In practice it may be desirable to implement less than the theoretical maximum number of multiplexed combinations available. Some of the practical reasons that may factor into the criteria for such a choice (which may be hard coded during design, or may alternately be left up to the instrument operator) may include: the desire to reduce the computational complexity required for a full implementation of the possible combinations; the desire to reduce the computational time required to perform a statistically acceptable analysis on the number of possible combinations; the desire to manufacture or to obtain a simpler, smaller, less costly instrument than would be needed for a full implementation of the theoretical maximum number of possible combinations; the desire for an operator to be able to operate the analytical platform with a minimum of specialized training; and the desire for a robust instrument designed to perform a reduced set of operations in a highly optimized fashion. Whichever the motivation, one may choose to produce a "sparse" multiplexed configuration, where some of the possible multiplexing choices have been removed.

In one embodiment of the present invention, such sparseness is introduced in the lifetime domain: Only a few of the possible lifetime bins are provided, the rest being removed and being replaced by gaps between the provided lifetime bins [e.g., removing bins $\tau_2$ (522) and $\tau_4$ (524) in FIG. 5].

The advantage of this configuration over a densely populated lifetime configuration is that the relative sparseness of the lifetime bins simplifies the process of digitally distinguishing the lifetime contributions of the remaining bins to the optical emission signal.

In another embodiment of the present invention, the sparseness of multiplexing is introduced in the spectral domain: Only a few of the possible wavelength bands are provided, the rest being removed and being replaced by gaps between the provided spectral bands [e.g., removing bands $FL_2$ (512) and $FL_4$ (514) in FIG. 5]. The advantage of this configuration over a densely populated spectral configuration is that the relative sparseness of the spectral bands simplifies the handling of any residual spectral overlap.

Figure 6:
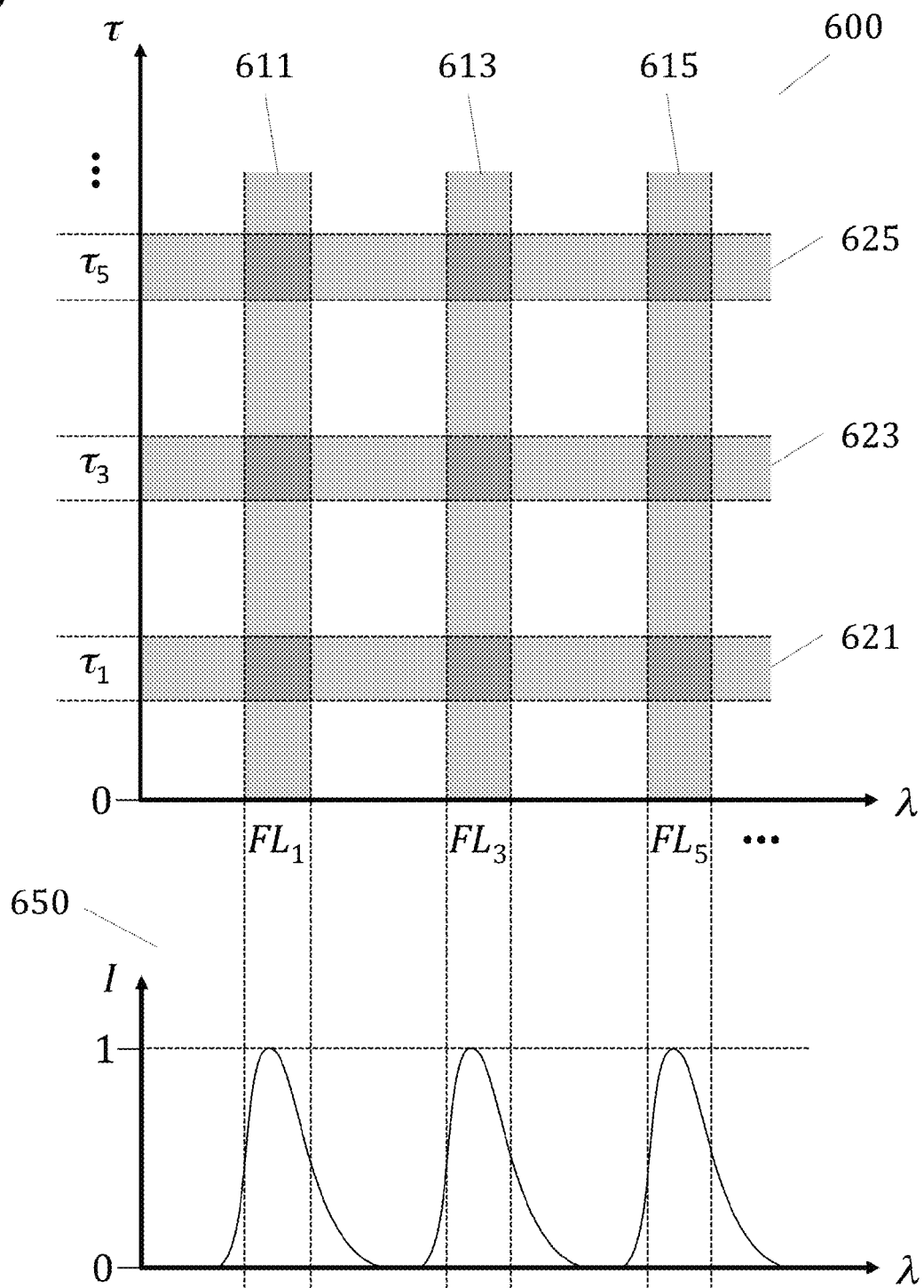
FIG. 6 is a wavelength-lifetime diagram coupled with a wavelength diagram illustrating a multiplexing approach sparse in both spectral bands and lifetime bins in accordance with one embodiment.

FIG. 6 shows an illustrative example (graph 600) of yet another embodiment of the present invention, where the sparseness of multiplexing has been introduced in both the spectral (graph 650 at bottom) and the lifetime domains simultaneously: Only a few of the possible wavelength bands have been provided, the rest having been removed and being indicated in the figure by the gaps between the provided spectral bands [e.g., between bands $FL_1$ (611) and $FL_3$ (613) and between bands $FL_3$ (613) and $FL_5$ (615)]; and only a few of the possible lifetime bins have been provided, the rest having been removed and being indicated in the figure by the gaps between the provided lifetime bins [e.g., between bins $\tau_1$ (621) and $\tau_3$ (623) and between bins $\tau_3$ (623) and $\tau_5$ (625)]. The resulting configuration, while having considerably fewer intersection points than the theoretical maximum, is however advantaged over a densely populated spectral and lifetime configuration by the reduction in the number of hardware components, the reduction in the complexity of the signal processing algorithms, by the relative increase in robustness and accuracy of the signal processing results, and by the relative simplicity of a training protocol for operation of the associated instrument platform.

Figure 7:
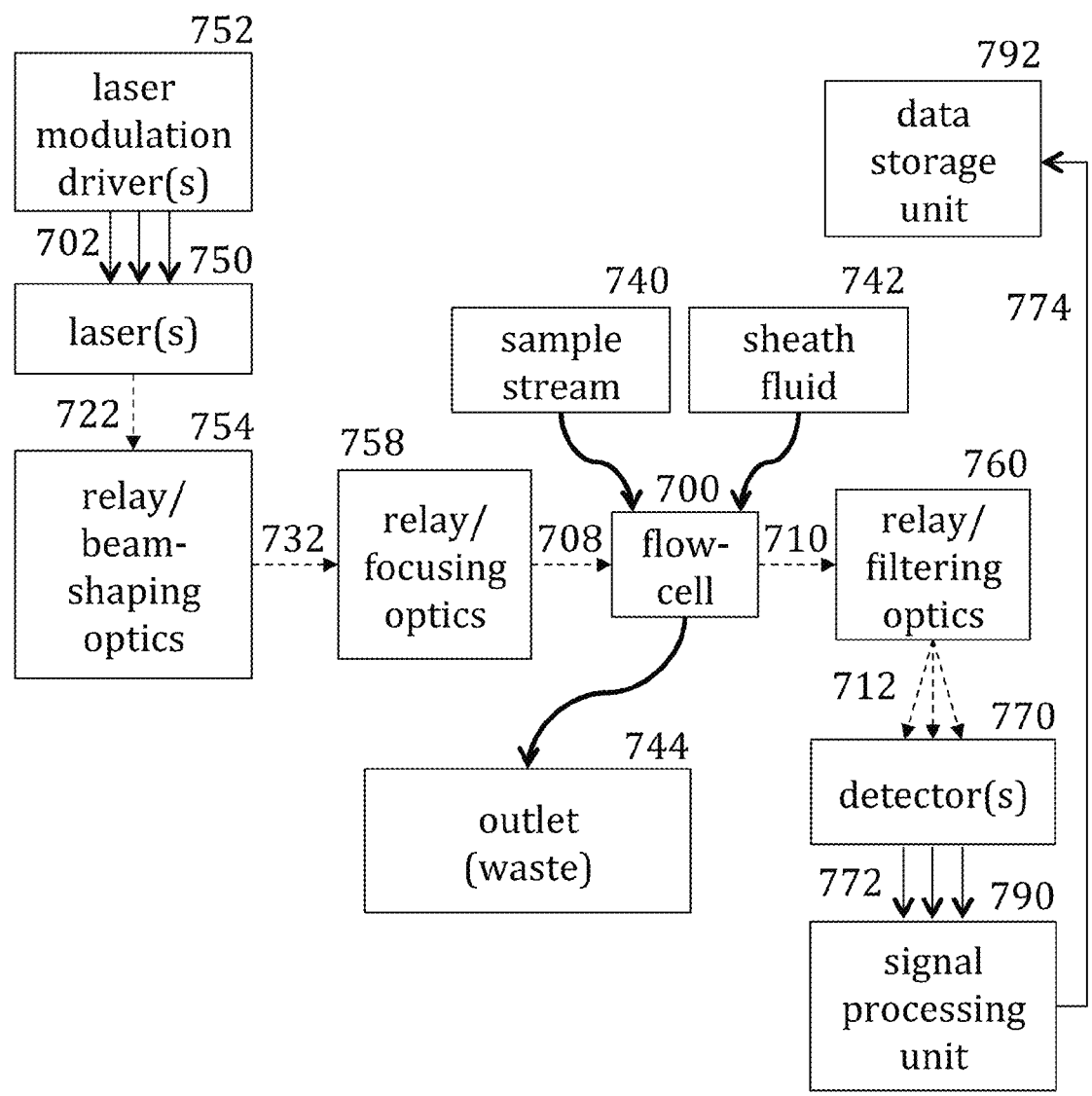
FIG. 7 is a schematic illustration of a system configuration of an apparatus for analysis of single particles in a sample in accordance with one embodiment.

FIG. 7 illustrates schematically a system configuration of an exemplary embodiment of the present invention, which provides an apparatus for highly multiplexed particle analysis in a sample. In another embodiment, it provides an apparatus for lifetime analysis of particles in a sample. One or more light source 750, e.g., a laser, produces one or more optical energy (light) beams 722 with desired wavelength, power, dimensions, and cross-sectional characteristics. One or more modulation drivers 752 provide modulation signal(s) 702 for the one or more respective light sources, resulting in the beam(s) 722 becoming pulsed. The modulation drivers may optionally be internal to the light source(s). The pulsed beam(s) are directed to a set of relay optics 754 (which can include, for instance, lenses, mirrors, prisms, or optical fibers), which may additionally optionally perform a beam-shaping function. Here relay optics will be intended to represent means to transmit one or more beams from one point in the system to another, and will also be intended to represent means to shape one or more beams in terms of dimensions and convergence, divergence or collimation. The output pulsed beam(s) 732 from the beam-shaping relay optics are directed to another optional set of relay optics 758 (which can include, for instance, lenses, mirrors, prisms, or optical fibers), which may additionally optionally perform a focusing function. The beam-shaping optics, the focusing optics, or both, may alternatively be incorporated into the light source module. The combined effect of the two sets of relay optics (the beam-shaping and the focusing sets) upon the input beam(s) from the light source(s) is to impart upon the beam(s) the desired output beam propagation characteristics suitable for interrogating particles. The second set of relay optics then directs the pulsed beam(s) 708 to the flowcell 700. The flowcell 700 provides for the passage of particles to be analyzed (which can include, for instance, cells, bacteria, exosomes, liposomes, microvesicles, microparticles, nanoparticles, and natural or synthetic microspheres) by conveying a sample stream 740 containing said particles as a suspension, and a stream of sheath fluid 742 that surrounds and confines said sample stream, as further described herein. An input portion of the flowcell focuses, e.g., by hydrodynamic means, the sample stream and the surrounding sheath stream to result in a tight sample core stream flowing through a microchannel portion of the flowcell, surrounded by sheath fluid. The tight sample core stream flowing past the interrogation region of the flowcell typically exposes, on average, less than one particle at a time to the beam or beams for interrogation (this is sometimes referred to in the art as "single-file" particle interrogation). The sheath fluid and the sample core stream are directed to a single outlet 744 (and generally discarded as waste) after passage through the interrogation portion of the flowcell. As the interrogating pulsed beam(s) of optical energy (light) interact with particles in the sample core stream by scattering, absorption, fluorescence, and other means, optical signals 710 are generated. These optical signals are collected by relay optics in box 760 (which can include, for instance, single lenses, doublet lenses, multi-lens elements, mirrors, prisms, optical fibers, or waveguides) positioned around the flowcell, then conveyed to filtering optics in box 760 (which can include, for instance, colored filters, dichroic filters, dichroic beamsplitters, bandpass filters, longpass filters, shortpass filters, multiband filters, diffraction gratings, prisms, or holographic optical elements) and then conveyed as filtered light signals 712 by further relay optics in box 760 to one or more detectors 770 (which can include, for instance, photodiodes, avalanche photodiodes, photomultiplier tubes, silicon photomultipliers, or avalanche photodiode microcell arrays). The detectors convert the optical signals 712 into electronic signals 772, which are optionally further amplified and groomed to reduce the impact of unwanted noise. The electronic signals are sent to an electronic signal processing unit 790 [which generally comprises a digitization front end with an analog-to-digital converter for each signal stream, as well as discrete analog and digital filter units, and may comprise one or more of a Field-Programmable Gate Array (FPGA) chip or module; a Digital Signal Processing (DSP) chip or module; an Application-Specific Integrated Circuit (ASIC) chip or module; a single-core or multi-core Central Processing Unit (CPU); a microprocessor; a microcontroller; a standalone computer; and a remote processor located on a "digital cloud"-based server and accessed through data network or wired or cellular telephony means], which executes further processing steps upon the electronic signals. The processed signals 774 are then sent to a data storage unit 792 (which can include, for instance, a read-only memory unit, a flash memory unit, a hard-disk drive, an optical storage unit, an external storage unit, or a remote or virtual storage unit connected to the instrument by means of a wired data or telecommunication network, a Wi-Fi link, an infrared communication link, or a cellular telephony network link). The stored or preliminarily processed data, or both, can also be made available to an operator for optional inspection of results.

Figure 8:
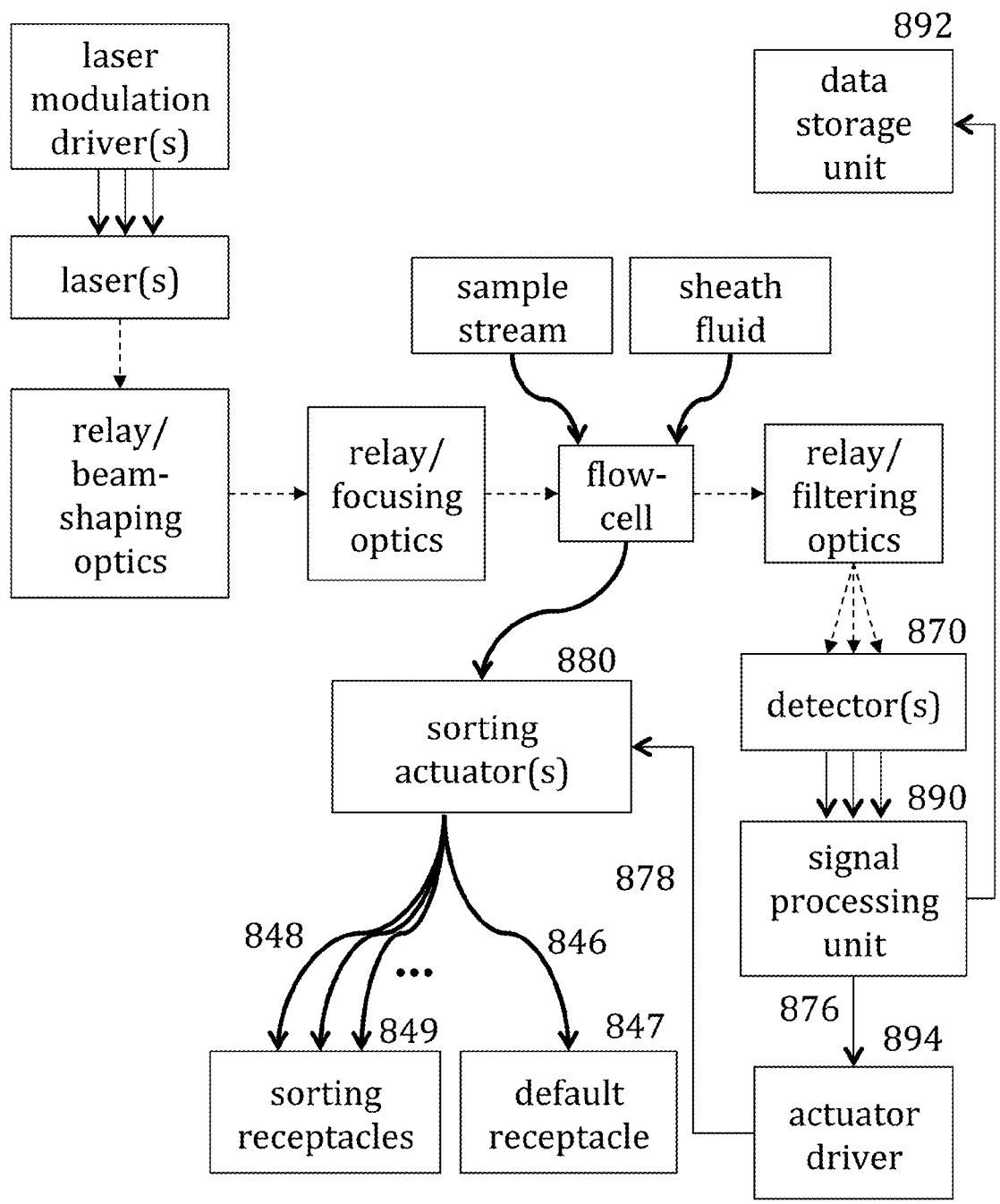
FIG. 8 is a schematic illustration of a system configuration of an apparatus for analysis and sorting of single particles in a sample in accordance with one embodiment.

FIG. 8 illustrates schematically a system configuration of an exemplary embodiment of the present invention, which provides an apparatus for highly multiplexed analysis and sorting of particles in a sample. In another embodiment, it provides an apparatus for lifetime analysis and sorting of particles in a sample. It is similar in configuration to the system configuration of FIG. 7, except in that it additionally provides for the capability to sort and collect particles based on their characteristics. The signal processing unit 890 generates in real time sorting control signals 876 based on the presence or absence or degree or nature of predetermined characteristics of the particles to be analyzed. For example, it may be desirable to identify and sort particles that, upon excitation by the interrogating pulsed light beam(s), emit fluorescence in a predefined spectral band at a level above a predefined threshold. As another example, it may be desirable to identify and sort particles that, upon excitation by the interrogating pulsed beam(s), exhibit fluorescence decay curve with a lifetime component in a certain range of values and at a percentage above a predefined threshold. Different criteria may be used in isolation or combined in compound logical forms (such as AND, OR, NOT, as well as more complex forms involving numerical comparisons of different quantities, such as "greater than," "less than," and so forth). The processing unit 890, once the processed signals from a given particle meet the predefined set of sorting criteria, triggers a signal 876 conveyed to an actuator driver 894. The actuator driver is an electronic control module connected to one or more sorting actuators 880. The sorting actuators may be positioned in, on, next to, or near the flowcell in the vicinity of, and downstream from, the interrogation region. One or more of the sorting actuators 880 is temporarily activated by drive signal 878 from the actuator driver 894 in response to the triggering signal 876 from the processing unit 890, resulting in a temporary diversion of the sample core stream, or of a portion of the sample core stream, away from the default sorting channel 846 and into one or more sorting channels 848. The default sorting channel 846 optionally directs the fluids it receives into a default receptacle 847. The sorting channel(s) 848 direct the sample core stream, in turn, to respective receiving sorting receptacle(s) 849. Once the temporary activation of one or more of the sorting actuators 880 is complete, the actuator(s) return to their resting state, and the sample core stream returns to its default sorting channel 846. The sorting actuator(s) 880 are controllable to achieve multiple actuation states, for instance, with an actuator driver 894, with a built-in control, with direct voltage or current control from the processing unit 890, or with electrical signals coming directly from logic circuitry connected with the one or more detectors 870.

Figure 9:
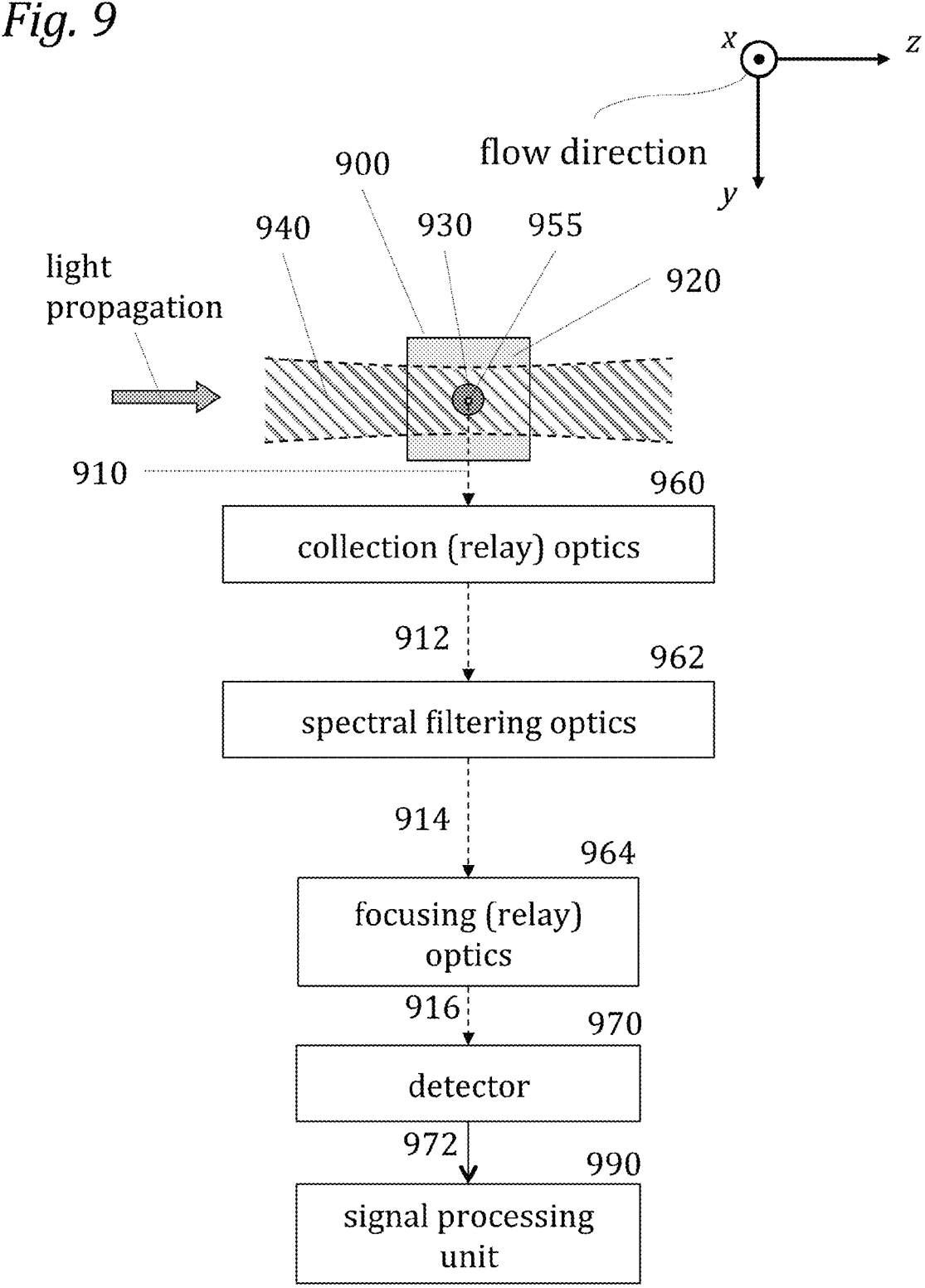
FIG. 9 is a schematic representation of the light collection and detection subsystem of a particle analyzer/sorter with a single spectral detection band in accordance with one embodiment.
Figure 10:
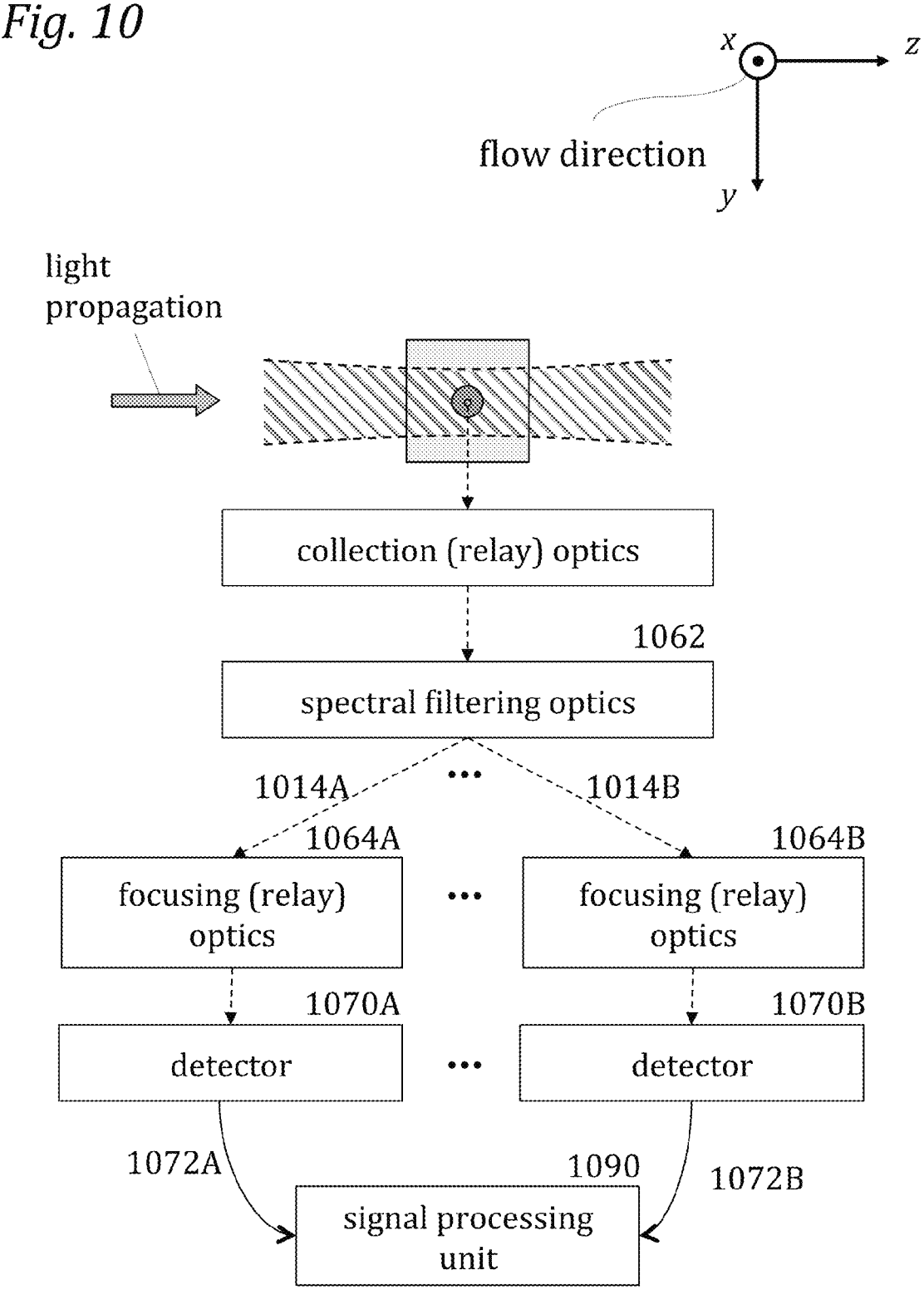
FIG. 10 is a schematic representation of the light collection and detection subsystem of a particle analyzer/sorter with multiple spectral detection bands in accordance with one embodiment.

In FIGS. 9 and 10, the relative orientation of fluid flow, light propagation, and transverse directions is shown, respectively, as the set of axes x, z, and y. The process steps involved in the performance of some embodiments of the present invention are described here in reference to FIGS. 9 and 10, and are also further summarized in flow-chart fashion in FIG. 18(a).

FIG. 9 illustrates a cross-section, perpendicular to the direction of fluid flow, of a possible light collection configuration of the present invention. A flowcell 900, of which the inner part is schematically indicated in the figure, provides a channel for fluid flow. Sheath fluid 920 is provided to confine the fluid 930 carrying particles 955 to be analyzed. The sheath fluid and the sample-carrying fluid are focused into the flowcell lumen, optionally by hydrodynamic means; such focusing produces a tight sample core stream bounded by the sheath fluid. An interrogating light beam or beams 940 are provided to interact with the particles in the sample core stream. The beam or beams, usually having a Gaussian intensity profile, are generally focused into a relatively tight spot in the plane of the sample core stream. Particles to be analyzed in the sample core stream interact with light in the beam or beams 940 to generate optical signals 910 by optical processes including, for instance, scattering, absorption, or fluorescence. The optical signals 910 are collected by collection optics 960. The collected optical signals 912 are then conveyed (relayed) to spectral filtering optics 962 to select appropriate spectral bands of the optical signals for detection. The spectral filtering optics 962 may be, for instance, reflective, transmissive, absorptive, diffractive, or holographic in nature or based on interference, or a combination thereof. The resulting spectrally filtered optical signals 914 are then conveyed (relayed) as signals 916 by focusing optics 964 to a detector 970. The detector converts the light signals 916 into electrical signals 972, which are then conveyed to a processing unit 990 for further analysis, processing, and optionally storage, as described above in reference to FIGS. 7 and 8 and as further discussed below. Together, the collection optics 960 and the focusing optics 964 may be referred to as relay optics.

In some embodiments, more than one spectral band output may be generated. For instance, FIG. 10 illustrates a cross-section, perpendicular to the direction of fluid flow, of another possible light collection configuration of the present invention. It is similar in concept to the configuration illustrated in FIG. 9 except that the spectral filtering optics 1062 produce more than one spectral band output 1014 (A and B), separated according to spectral characteristics. Each spectral band is then conveyed (relayed) to a separate set of focusing optics 1064 (A and B) and separate detectors 1070 (A and B), resulting in respectively separate electrically converted signals 1072 (A and B). The resulting electrical signals are then routed to signal processing unit 1090 for further elaboration. FIG. 10 depicts, for the sake of clarity, two sets of spectral bands, focusing optics, and detectors; it will be apparent to those skilled in the art that an arbitrary number of such sets is encompassed by the scope of the invention.

The process steps described below in conjunction with FIGS. 11(a)-(f), 12(a) and 12(b) are also summarized in a flow-chart fashion in FIG. 18(c).

Figure 11:
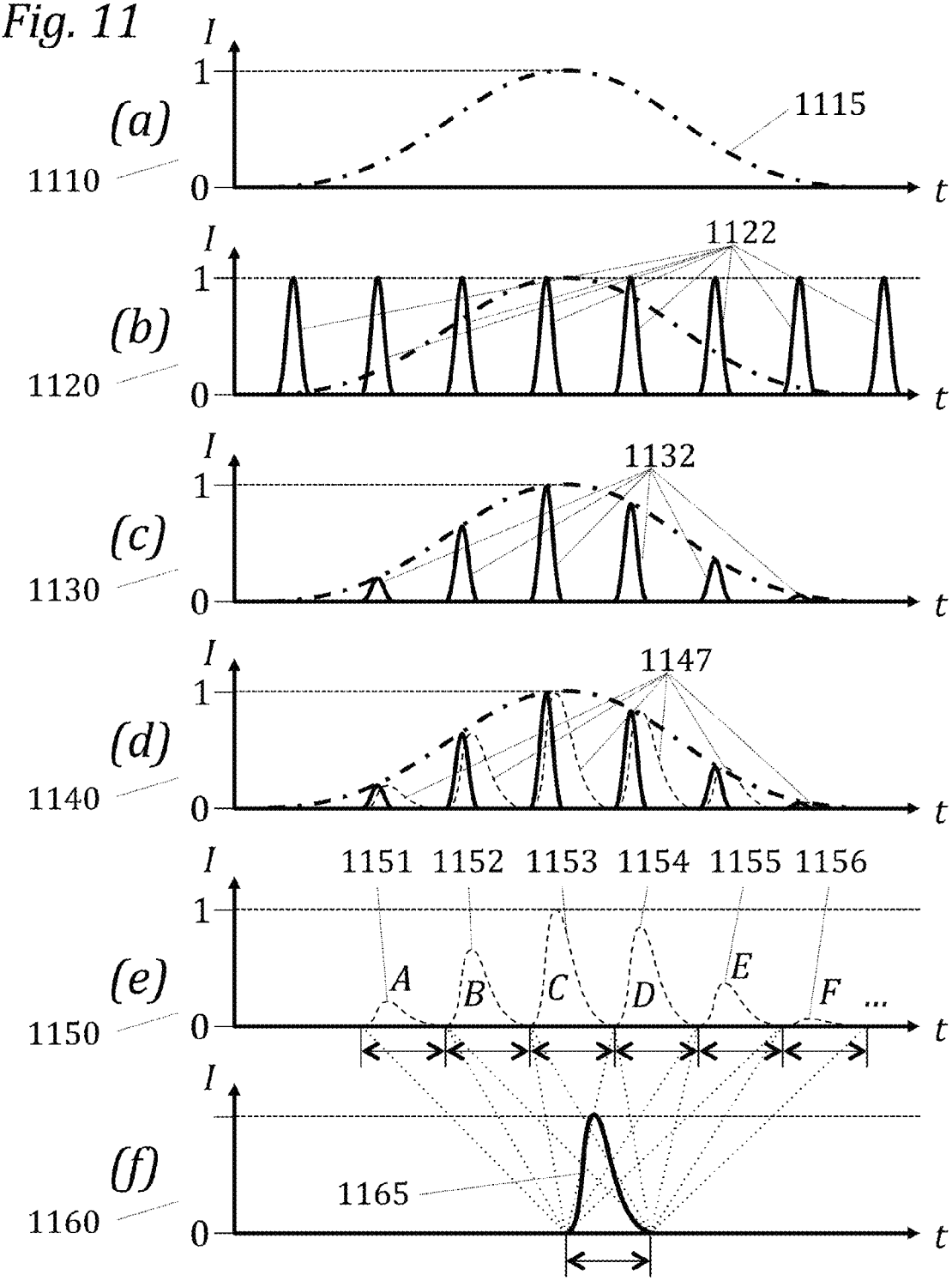
FIG. 11 is a time-domain diagram illustrating a signal processing sequence in accordance with one embodiment: (a) interaction envelope due by a flowing particle crossing the beam; (b) excitation pulses; (c) effective excitation pulses; (d) fluorescence emission pulses with decay curves; (e) segmentation of individual pulse signals; (f) construction of a supercurve.

FIG. 11 illustrates, for the specific case of implementation of the present invention on a flow cytometry platform, the principles involved in excitation, emission, detection, and analysis of fluorescence lifetime signals from particles under analysis. The various panels of the figure will be referred to in the text that follows to better illustrate the various steps of the signal transduction process. In each panel (a)-(f), a graph depicts the evolution over time (t) of certain optical intensities (I). In every case except where noted, the optical intensities are each normalized to unit peak values.

The graph 1110 in FIG. 11(a) depicts the canonical behavior of the optical signals resulting from the interaction between an always-on excitation light source (also referred to in the art as a constant-wave, or cw, source) and a particle passing through the region of interrogation (typically in a flow cell or other component having a similar function). As the particle enters, then exits, the region of interrogation, the excitation interaction signal (the dash-dotted line 1115) rises then falls, in concert with the spatial profile of the light beam used for interrogation, as measured along the line of passage of the particle. The particle, in this canonical pedagogical illustration, is assumed small in comparison with the dimension of the light beam along the direction of passage of the particle; modifications to this framework that generalize this to the case of particles of arbitrary size are possible but are not informative for the purpose at hand, and are not taken up here. A typical light beam having dimensions, along the line of passage of particles to be analyzed, from less than 10 to more than 100 microns, and a typical flow cytometer causing particles to pass through the region of interrogation at flow velocities of below 0.1 to more than 10 m/s, the range of possible durations of the excitation interaction envelopes, as the shape of curve 1115 in FIG. 11(*a*) is sometimes referred to, is quite wide, stretching from less than 1 us to more than 1 ms. However, in most cases in current practice the full-width at half-maximum (FWHM) of the excitation interaction envelope is around a few microseconds.

The graph 1120 in FIG. 11(*b*) juxtaposes, for illustrative purposes, the canonical interaction envelope 1115 from FIG. 11(*a*) (the dash-dotted line) with one possible configuration of excitation pulses from a modulated source of optical energy. The pulses are shown in a train of uniformly repeated, essentially identical units (the sharp features 1122 in thick solid lines); each pulse is short as compared to the FWHM of the canonical interaction envelope, and each pulse is separated from neighboring pulses by a time generally larger than the width of the pulses themselves. One key aspect of the invention captured in this panel 11(*b*) is that the modulation of the optical energy source (or sources) should result in a series of essentially identical pulses, each short compared to the typical interaction time, and each well separated from the next.

The graph 1130 in FIG. 11(*c*) depicts the prophetic result of delivering the train of excitation pulses 1125 illustrated in FIG. 11(*b*) to a particle flowing in a flow cell according to design and operating parameters typical of flow cytometer constructions known in the art. The resulting excitation interactions are shown as a series of pulses of varying height (features 1132 in thick solid lines) conforming to an overall envelope (the dash-dotted line), said envelope corresponding to the interaction envelope that would result, were the light beam continuous instead of pulsed and all other things remaining equal. While the details of the interaction sequence would, generally, vary from particle to particle [for example, the detailed timewise location of the individual interaction pulses 1132 in FIG. 11(*c*) under the overall envelope is a function of the relative timing of the pulse train with respect to the arrival of the particle], the general nature of the excitation interaction as consisting of a series of pulses modulated by a "carrier" envelope is determined by the design and operating parameters of the apparatus. In this graph 1130 of FIG. 11(*c*) the individual interaction pulses are not normalized to unit intensity.

The graph 1140 in FIG. 11(*d*) adds another key element of the current invention to the picture, namely the ability to measure the temporal evolution of the fluorescence decay curves. The overall carrier envelope (dash-dotted line) and the individual excitation interaction pulses (features in thick solid lines) are as illustrated in FIG. 11(*c*). The fluorescence decay curves are shown as thin dashed lines 1147. Each fluorescence decay curve follows directly the optical excitation associated with the interaction pulse immediately preceding it. It can be appreciated that the fluorescence decay curves are, generally, asymmetric: While the rising portion is dominated by the absorption of optical energy from the excitation source, the waning portion (the decay) is driven by the quantum mechanical processes of fluorescence emission, which vary from molecule to molecule and are additionally affected by the molecular microenvironment, and generally result in a curve with a longer decay-side tail. In this graph 1140 of FIG. 11(*d*) the individual interaction pulses and the individual fluorescence decay curves are not normalized to unit intensity.

It is a fundamental property of linear functions that the shape of a curve is unaffected by an arbitrary constant scaling factors: for example, a Gaussian bell curve will remain a Gaussian bell curve no matter what fixed multiplicative scaling factor may be applied to it. A corollary of this is that if two curves are generated by the same function, an appropriate choice of a scaling factor can be found which, applied to one curve, turns it into the other one. Since the same lifetime processes are at work in each of the decay curves of graph 11(*d*), they can be normalized to unit peak intensity. This optional normalization step does not affect the nature of the decay (i.e., it leaves the decay time constant, or lifetime, unaffected) while bringing all of the curves on the same scale for ease of comparison. In some cases, depending on the nature and degree of noise present on the signal, the normalization step is omitted to achieve the best results; the rest of the process is illustrated here with this normalization step omitted.

The next process step in the lifetime analysis algorithm involves segmenting the signal sequence into individual decay curves. The dashed curves 1147 in graph 1140 of FIG. 11(*d*) represent optical emission signals, such as, e.g., fluorescence decay curves; these optical signals are detected by one or more detectors, converted into electrical signal, and digitized for further processing. In graph 1150 of FIG. 11(*e*) the sequence of pulse signals (dashed curves, representing digitized electrical signals corresponding to the optical signals they are converted from) is broken mathematically into individual pulse signal segments 1151-1156 (A, B, C, . . . ) while maintaining a consistent phase across the entire sequence; that is, a selected feature of each pulse (e.g., the peak, the midpoint of its rising edge, etc.) is chosen as the reference, and the sequence is cut up into equal segments [shown below the axis in FIG. 11(*e*)], all consisting of substantially the same number of digitization elements, and all starting substantially the same number L of digitization elements to the left of the respective reference point, such number L being chosen to result in segments, each of which (whenever possible) contains an entire decay curve not split between adjacent segments, as illustrated schematically in FIG. 11(*e*). The segment length is chosen to closely match the excitation pulse repetition period.

Graph 1160 in FIG. 11(*f*) depicts the following step of signal processing by showing each of the decay curve segments 1151-1156 from FIG. 11(*e*) (A, B, C, . . . ) added coherently on top of each other, with the respective temporal relationships within each segment unchanged. Such adding is performed coherently on the basis of individual digitization elements: The values of the first digitization index (#0) in every segment are added together (A0+B0+C0 . . . ), the values of the second digitization index (#1) in every segment are added together (A1+B1+C1 . . . ), and so on for all digitization indices in all segments. The result is a "supercurve" [bold curve 1165 in FIG. 11(*f*)], where each digitization index has a value equal to the sum of all the corresponding digitization indices from all segments. The supercurve is then converted to a semilog scale for further processing.

This signal processing method removes incoherent noise contributions from the result while boosting the contribution of signals coherent from pulse to pulse. The supercurve 1165 in graph 1160 of FIG. 11(*f*) may still exhibit some degree of incoherent noise, which is to be expected given the stochastic nature of the decay process and the presence of various sources of measurement noise on the signals; however, the general nature of the decay is expected to remain constant within a given population of fluorophores, and the supercurve process is aimed at maximizing the signal from such common decay while minimizing the effect of stray light signals, electronic noise and other events lacking information content germane to the analysis being carried out.

Figure 12:
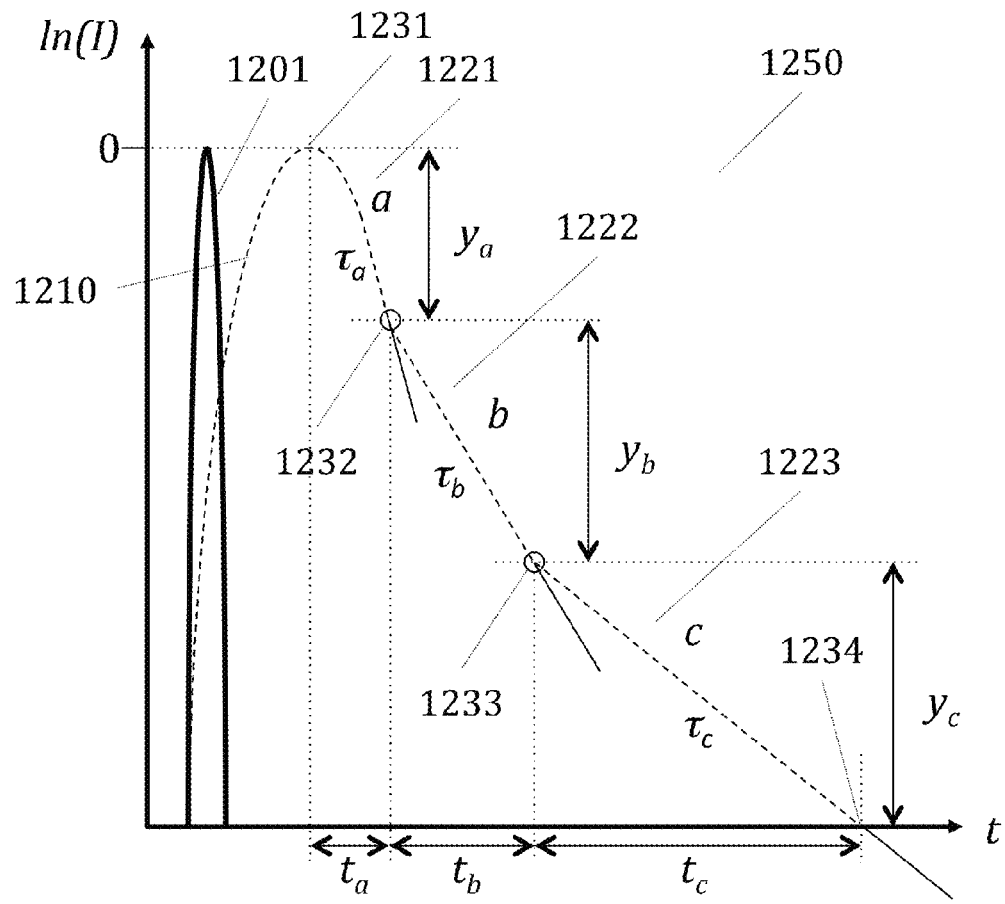
FIG. 12(a) is a log-linear time-domain diagram illustrating a triple-exponential decay supercurve constructed from individual pulse signals resulting from pulsed excitation.
FIG. 12(b) is a log-linear time-domain diagram illustrating the process of computing successive index-pair differences, determining supercurve knee points, and determining supercurve time-constant branches.
Figure 12:
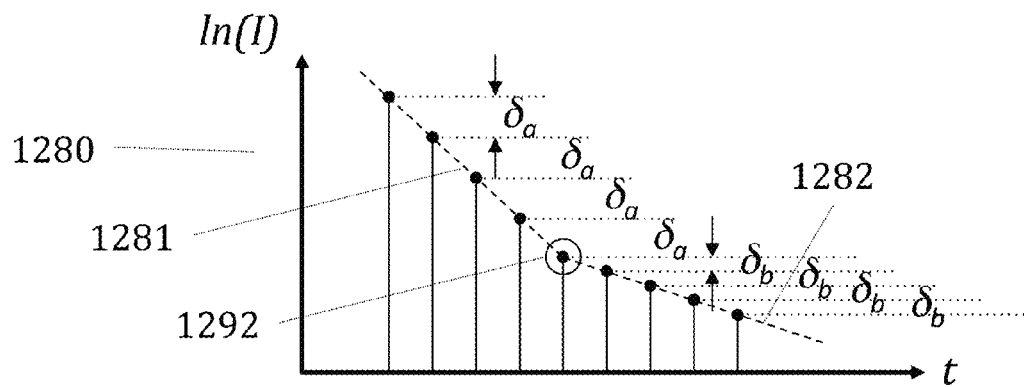

FIGS. 12(a) and 12(b) illustrate exemplary embodiments of several steps of an analysis method of the current invention. Both FIGS. 12(a) and 12(b) display curves plotted on a semilog scale of the natural (or, alternatively, the base-10) logarithm axis of measured intensity vs. the linear axis of time. In graph 1250 of FIG. 12(a) the excitation pulse (bold solid curve 1201) and the resulting emission supercurve due, e.g., to fluorescence (dashed curve 1210) are each normalized to unity peak value; on the shown logarithmic scale, a linear value of one corresponds to the logarithmic value of zero. The supercurve 1210 shown is obtained as described above in reference to FIGS. 11(a)-(f) for supercurve 1165. For illustrative purposes, the supercurve 1210 in graph 1250 of FIG. 12(a) is shown as comprising three distinct lifetime components [each also referred to herein as "component," "lifetime," "lifetime value," "1/e value," "time constant," "decay constant," or "exponential decay", and corresponding to the value of T in the standard exponential decay formula $I(t)=I_0 \exp(-t/\tau)$, where $I_0$ is the starting intensity and $I(t)$ is the intensity after a time t]: $\tau_a$, $\tau_b$, and $\tau_c$. In this example, $\tau_a$ is the smallest time constant of the three, $\tau_c$ is the largest, and $\tau_b$ is intermediate between the two. The relative values of $\tau_a$, $\tau_b$, and $\tau_c$ are reflected in the slopes of the three branches a (1221), b (1222), and c (1223) of the supercurve 1210: the slope of branch a 1221 is steepest, the slope of branch c 1223 is mildest, and the slope of branch b 1222 is intermediate between the two. The slope of a branch on a semilog plot of the kind depicted in FIGS. 12(a) and 12(b) is inversely proportional to the value of the corresponding time constant. The three branches 1221-1223 of the supercurve 1210 in FIG. 12(a) are defined as follows: The first branch a 1221 begins at the peak 1231 of the supercurve and ends at the first "knee" 1232 of the supercurve (where by "knee" is meant a substantial change in slope, indicated by an open circle); the second branch b 1222 begins at the first knee 1232 and ends at the next knee (the next open circle 1233); the third branch c 1223 begins at this next knee 1233 and ends at 1234 where the supercurve meets the measurement noise floor (schematically indicated in FIG. 12(a) by the time axis t). The slope of each branch is defined as customary as the ratio of the ordinate and the abscissa over a portion of or the entire branch: e.g., for branch b, the slope value is $s_b=y_b/t_b$. The time constant corresponding to such slope is then obtained by the reciprocal of the slope: $\tau_b=1/s_b$.

It will be appreciated that when dealing with real measurements subject to, for instance, noise, background, uncertainty, instrument error or drift, component variability, and environmental effects, there may be departures, sometimes substantial, from the illustrations and depictions presented here. Even when such effects are low or minimized, other effects may act to mask, distort, alter, modify, or otherwise change the relationships among the various mathematical and physical quantities mentioned here. As one example, the noise floor where the supercurve in FIG. 12(a) starts and ends may be higher in certain cases and lower in others, depending on several factors, including the ones just mentioned. The variability in the noise floor may affect the determination of one or more of the slopes of the branches of the supercurve. Likewise, the precise location of a knee between two branches on the supercurve may be subject to uncertainty depending on the level of residual noise on the supercurve. Another example of the distortion created by physical effects is shown in FIG. 12(a) where branch a 1221 is shown as beginning at the peak 1231 of the supercurve 1210, however the slope of this first branch does not immediately converge onto a stable value due to the roll-off from the peak. The degree of roll-off is dependent on the shape of the excitation pulse, the value of the first-branch lifetime, and other factors. These effects notwithstanding, it is one object of the present invention to minimize the impact of such effects. Construction of the supercurve from a number of individual pulse signals, with its attendant improvement in signal to noise, is one element that contributes to such minimization.

Another element is the relative simplicity in the extraction of desired parameters, such as the values of the time constants, from a supercurve. This is illustrated by graph 1280 in FIG. 12(b). Graph 1280 shows a detail 1211 of the supercurve 1210 of FIG. 12(a), where branch a 1281 (corresponding to branch a 1221 in graph 1250) ends and branch b 1282 (corresponding to branch b 1222 in graph 1250) begins. (The graph has been offset and rescaled in both abscissa and ordinate for illustrative purposes.) The two branches meet at the knee 1292 indicated by the open circle, corresponding to knee 1232 in graph 1250. Also plotted in FIG. 12(b) are the individual digitized points of the supercurve, indicated by small filled circles with solid drop lines to the time axis. The process step of determining the location of a knee (that is, the transition between one branch where a value of lifetime dominates, to another branch where a different value of lifetime dominates) comprises computing differences between successive values of the digitized supercurve. Four such difference for branch a are shown as $\delta_a$. Where residual noise on the supercurve is minimized, the value of $\delta_a$ from digitized point pair to digitized point pair will show little variation. Once the knee is crossed, however, the next computed difference will jump to $\delta_b$, and successive differences will once again remain substantially uniform around this new value. For one of the main objectives of the present invention, namely the provision of highly multiplexed means of particle analysis and sorting, it is not critical that the depicted successive values of $\delta_a$ be rigorously constant, nor those of $\delta_b$; it is merely sufficient that $\delta_a$ be different enough from $\delta_b$ to enable detection of the slope change at the indicated knee point. Sufficient difference between $\delta_a$ and $\delta_b$ is related to the precision and accuracy of the measurement system, the number, types, and severity of noise or error sources, and other factors. Detection of a discontinuous change in slope, however, is intrinsically simpler, instrumentally and computationally, than the absolute determination of the value of a slope.

Once a knee is found, the process continues until the entire supercurve is examined. The location of each knee, together with the location of the start of the first branch and the end of the last branch, define all the branches of the supercurve. The next processing step involves computing the average slope for each branch, which was described above in reference to FIG. 12(a), and from such slope values the time constants of each branch are calculated. The following processing step involves allocating each branch to one of a set of predetermined lifetime (or time constant) bins. As illustrated in FIGS. 5 and 6, one aspect of the present invention is the provision of a limited set of lifetime bins, where the lifetime within any one bin is allowed to vary somewhat, as long as the variation is not greater than the difference between neighboring bins. For the purpose of analyzing a supercurve and determining what lifetimes gave rise to the signals from which the supercurve was constructed, it is sufficient to establish (1) which of the lifetime bins was present in the measured particle or event (i.e., what fluorophores or other molecular species were present with a fluorescence decay value within the range of any one of the provided lifetime bins), and (2) the degree of relative contribution of each detected lifetime. For (1), the set of time constants computed from the branches of the supercurve as described above is compared to the set of allowed lifetime bins. In some cases there will be as many separate detected branches in a supercurve as there are bins: this would be the case for FIG. 12(a), for example, if the number of allowed bins were 3. In other cases there will be fewer branches, indicating that a certain bin was not present (i.e., that no fluorophore or molecular species with a lifetime in the range of values of that bin was detected). By comparing the set of measured time constants with the set of allowed bins, a determination is made as to which bins are present in the measurement. Determination of the relative contribution of each detected lifetime (now associated with one of the allowed lifetime bins) is performed by comparing the values of the ordinates of each branch [the values $y_a$, $y_b$, and $y_c$ in graph 1250 of FIG. 12(a)] with a calibration look-up table generated during manufacture of the apparatus. Such calibration look-up table is created by generating supercurves with known inputs, i.e., with 100% of one lifetime bin, 100% of another, and so on for all the lifetime bins selected to be available on the apparatus; then with varying mixtures of bins, such as, e.g., 10% of bin 1 and 90% of bin 2, 20% of bin 1 and 80% of bin 2, and so on until 90% of bin 1 and 10% of bin 2; repeating this for each pair of bins available on the apparatus. The resulting data provides the look-up table to compare measured lifetime ordinates (e.g., $y_a$, $y_b$, and $y_c$) with, and thereby determine the relative contributions of each detected lifetime.

Figure 13:
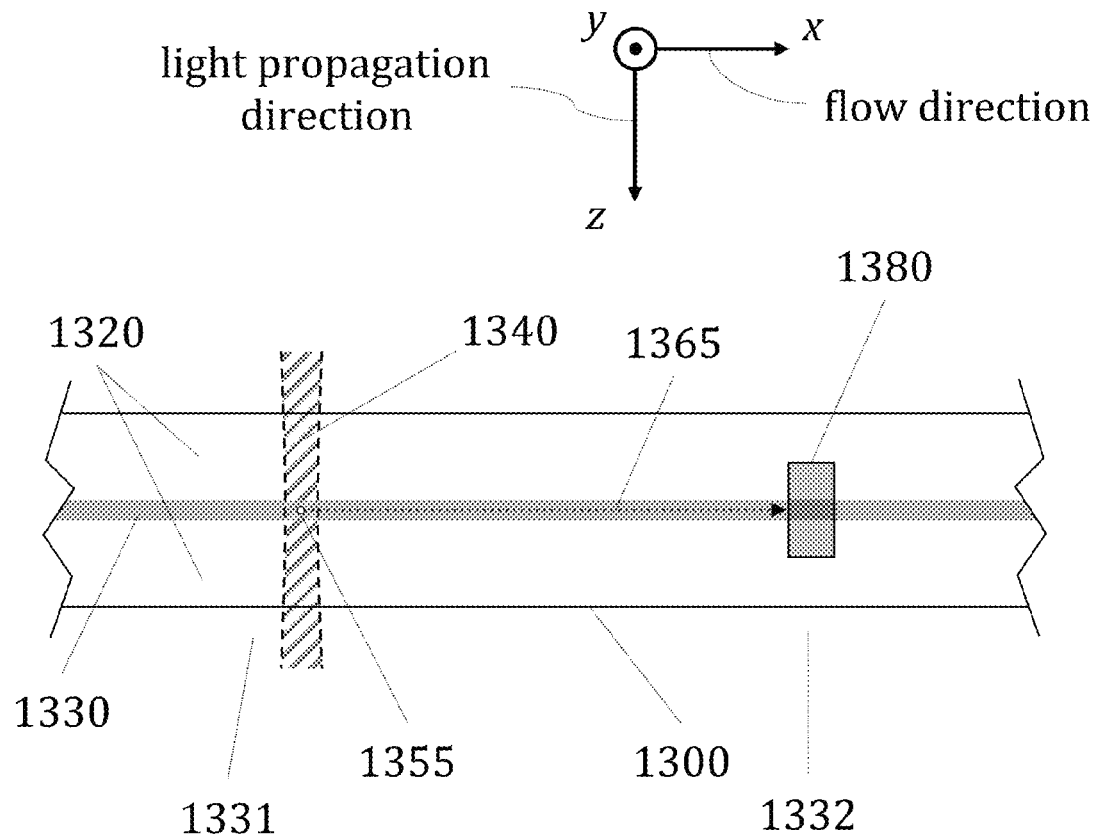
FIGS. 13(a) and (b) are schematic plan-view illustrations of two steps, or states, of a particle analysis/sorting method that uses a sorting actuator in accordance with one embodiment.
Figure 13:
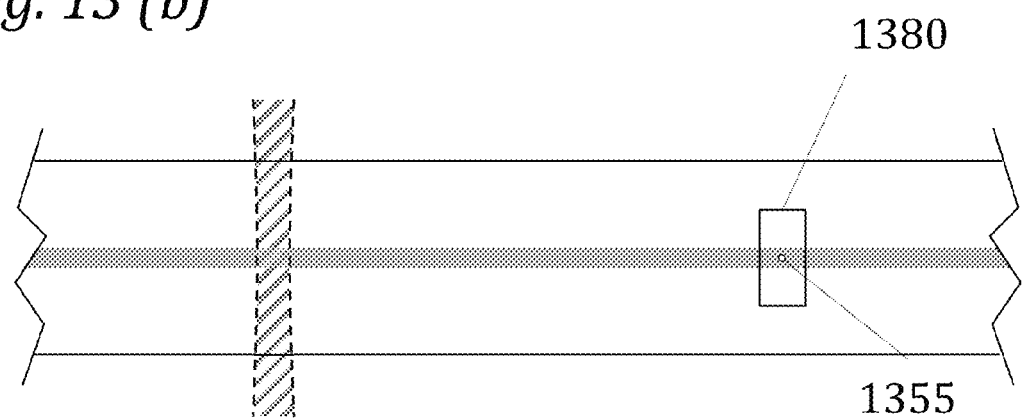

FIGS. 13(a) and 13(b) illustrate exemplary embodiments of two steps of an analysis and sorting method of the current invention. In FIGS. 13(a) and (b), the relative orientation of fluid flow, light propagation, and transverse directions is shown as the set of axes x, z, and y, respectively. The assignment of the axes and directions is similar to that in FIGS. 9 and 10, however the orientation of the axes with respect to the page is rotated as compared to FIGS. 9 and 10, with the light propagation and flow directions being in the plane of the page in FIGS. 13(a) and (b). Each of the two figures shows a schematic representation of a side view of the interrogation region 1331 and sorting region 1332 of the flowcell 1300. The focusing region of the flowcell, if provided, e.g., by hydrodynamic means, is to the left of the picture; the sample core stream 1330, surrounded by the sheath fluid 1320, comes in from the left and flows towards the right. The sheath fluid 1320 is bounded by the inner walls of the flowcell 1300, and the sample core stream 1330 is bounded by the sheath fluid 1320. In the interrogation region 1331 at left, one or more beams of pulsed optical energy 1340 are delivered to the flowcell by relay/focusing optics and intersect the sample core stream 1330. In the sorting region 1332 at right, one or more actuators (shown in the picture as actuator 1380) are provided in contact with or near the flowcell, positioned in such a way as to overlay the position of the sample core stream 1330.

FIG. 13(a) shows a first time step in the processing of a sample whereby a single particle 1355 in the sample core stream 1330 enters the interrogation region 1331 (where the beam or beams 1340 intersect the sample core stream 1330). The light-particle interaction generates light signals as described above in reference to FIG. 9 or 10, which light signals are collected and relayed to one or more detectors. The detector(s) record the optical interaction signals generated by the particle 1355, and convey that information to the signal processing unit as illustrated schematically in FIG. 8. As described above in reference to FIG. 8, the processing unit uses that information to produce, if certain predetermined criteria are met, a triggering signal for an actuator driver, which driver in turn activates the actuator 1380 in FIG. 13(a). FIG. 13(b) shows a second time step in the processing of the sample whereby the particle 1355 detected in the step depicted in FIG. 13(a), after following path 1365 in the flowcell along direction x, arrives at a point in the vicinity of the actuator 1380 in the sorting region 1332 of the flowcell. The design of the flowcell, of the optical layout of the actuator, and of the detection, processing, and control electronics is such that the actuator is activated as such a time when the passing particle is calculated, estimated, predicted, or found, upon calibration or determined empirically during instrument design or assembly, to be nearest to a position where activation of the actuator results in the desired diversion of the core stream to one of the one or more sorting channels. The timing of the triggering signal (i.e., the relative delay from particle detection to sorting actuation) is designed to take into account both the average velocity of fluid flow in the flowcell and its spatial profile across the flowcell cross-section, according to the characteristics of Poiseuille flow known in the art and as modified based on empirical or modeling information.

In FIGS. 14(a) and (b), 15(a) and (b), 16(a) and (b), and 17(a)-(d), the relative orientation of fluid flow, light propagation, and transverse directions is shown as the set of axes x, z, and y, respectively. The assignment of the axes and directions is similar to that in FIGS. 9 and 10, however the orientation of the axes with respect to the page is rotated as compared to FIGS. 9 and 10, with the fluid flow and transverse directions being in the plane of the page in FIGS. 14(a) and (b), 15(a) and (b), 16(a) and (b), and 17(a)-(d). The cross-sectional plane depicted in FIGS. 14(a) and 14(b), 15(a) and (b), 16(a) and (b), and 17(a)-(d) is the plane that contains the sample core stream.

Figure 14:
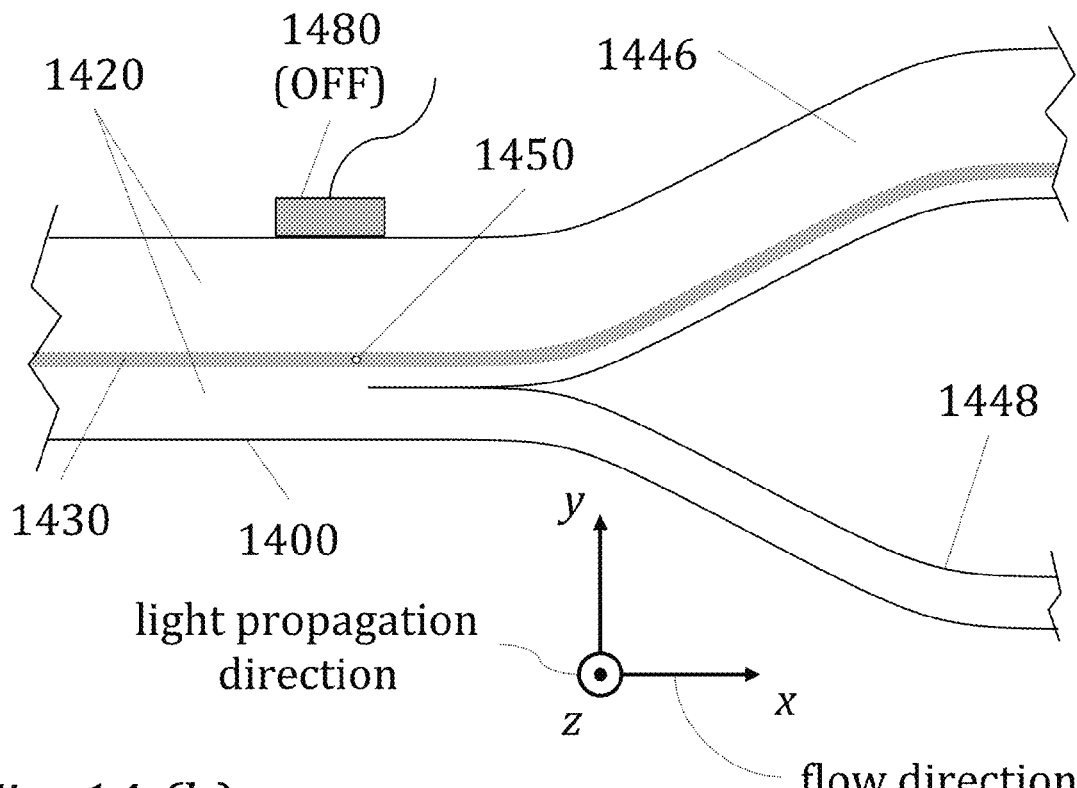
FIGS. 14(a) and (b) are schematic cross-sectional illustrations of two steps, or states, of a particle analysis/sorting method with two sorting states and one-sided actuation in accordance with one embodiment.
Figure 14:
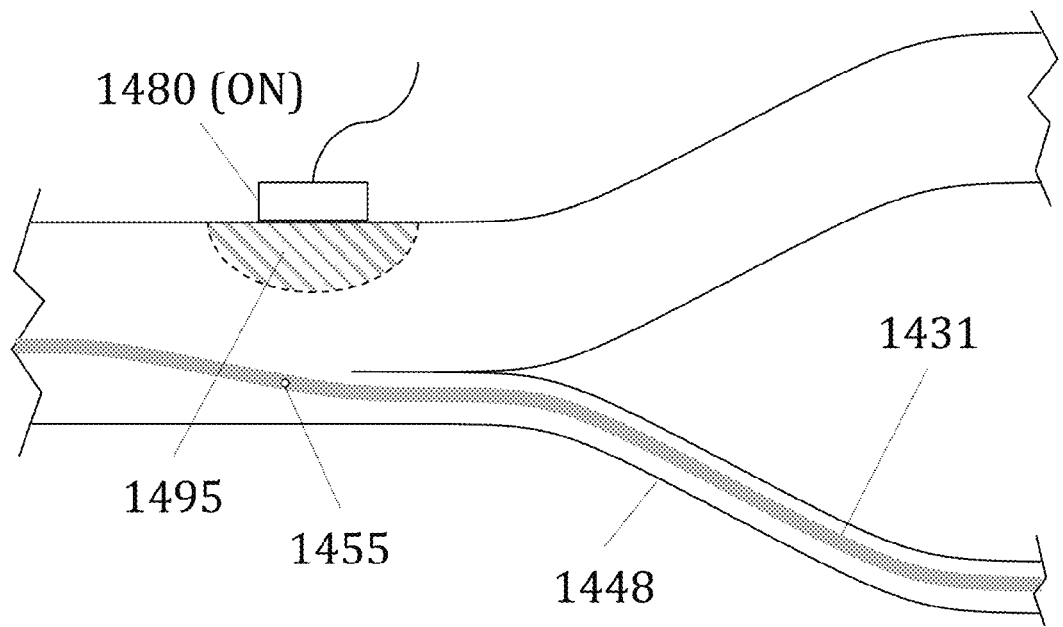

FIGS. 14(a) and 14(b) illustrate one embodiment of two states of the particle analysis and sorting method of the current invention. Each of the two figures shows a schematic representation of a cross-sectional view of the sorting region of the flowcell. Similarly to the situation depicted in FIGS. 13(a) and (b), the focusing region of the flowcell, e.g., by hydrodynamic means, if provided, is to the left of the picture; the sample core stream 1430, surrounded by the sheath fluid 1420, comes in from the left and flows towards the right. The sheath fluid 1420 is bounded by the inner walls of the flowcell 1400, and the sample core stream 1430 is bounded by the sheath fluid 1420. The flowcell 1400 splits into two channels in the sorting region: the default sorting channel 1446 and the sorting channel 1448. Actuator 1480 is depicted as embodied in, in contact with, or in proximity of the inner wall of the flowcell 1400 on the default sorting channel side. FIG. 14(a) shows the configuration of the default state, where with the actuator 1480 in the OFF state, a non-selected particle 1450 in the sample core stream 1430 flows by design into the default sorting channel 1446. Similarly to the state depicted in FIG. 13(b), FIG. 14(b) shows the configuration of the sorting state, where with the actuator 1480 in the ON state, a transient gas, vapor, or gas-vapor bubble, or a region of heated or cooled, less-dense sheath fluid 1495 is generated (by means including, for instance, thermal means, electrolytic means, and gas injection means), which creates a localized flow diversion in the depicted cross-sectional plane and in its vicinity, which diversion temporarily deflects the sample core stream 1431 into the sorting channel 1448, which sample core stream contains a particle 1455 detected upstream and automatically selected by analysis algorithms to trigger sorting actuation. Following deactivation of the actuator 1480, the transient gas, vapor, gas-vapor bubble or region of less-dense fluid 1495 shrinks or is cleared away, and the flow pattern returns to the original default state of FIG. 14(*a*).

Figure 15:
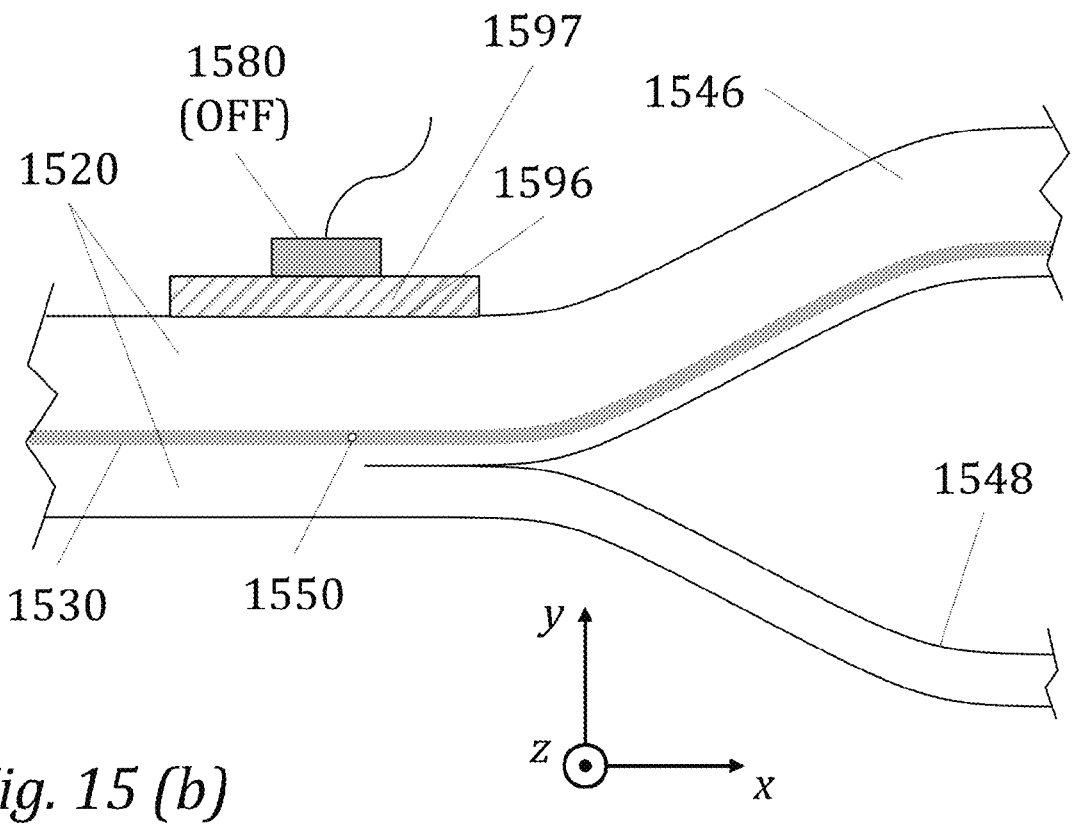
FIGS. 15(a) and (b) are schematic cross-sectional illustrations of two steps, or states, of a particle analysis/sorting method with two sorting states and one-sided actuation in accordance with one embodiment.
Figure 15:
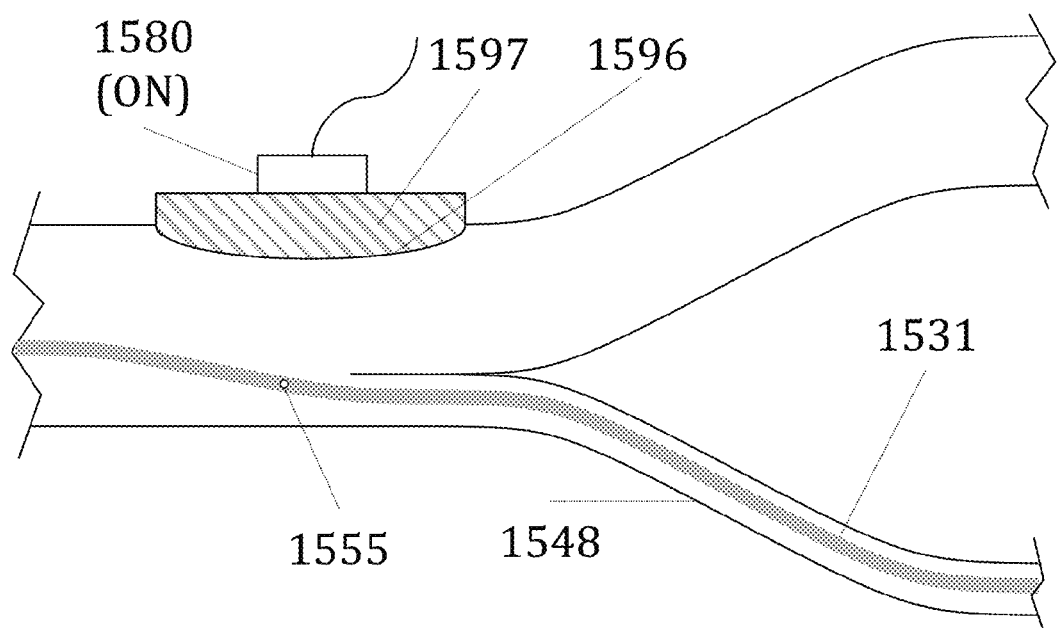

FIGS. 15(*a*) and 15(*b*) illustrate another embodiment of two states of a particle analysis and sorting method of the current invention. It is similar to the embodiment illustrated in FIGS. 14(*a*) and 14 (*b*), except in the design and nature of actuation. Here the actuator 1580 is located in proximity to an expandable chamber 1597 adjacent to the flowcell inner wall and separated from the sheath fluid 1520 by a flexible membrane 1596. With the actuator 1580 in the OFF or default state as shown in FIG. 15(*a*), the expandable chamber 1597 is in its default configuration at a pressure designed to match the pressure of the fluid inside the flowcell at the location of the membrane, resulting in a flat shape of the membrane to match the shape of the flowcell inner wall, and a non-selected particle 1550 in the sample core stream 1530 flows by design into the default sorting channel 1546. With the actuator 1580 in the ON or sorting state as shown in FIG. 15(*b*), the expandable chamber 1597 is pressurized (by means including, for instance, thermal means, mechanical means, hydraulic and gas injection means) to a higher pressure than in the default configuration; this pressure differential causes the membrane 1596 to flex into the flowcell until a new equilibrium is reached. The bulging membrane causes the flow pattern to shift in a similar way to that previously shown for FIG. 14(*b*), resulting in the sample core stream 1531 being temporarily diverted into the sorting channel 1548, which sample stream contains a particle 1555 detected upstream and automatically selected by analysis algorithms to trigger sorting actuation. Following deactivation of the actuator 1580, the expandable chamber 1597 is allowed to or made to return to its default pressure state, the membrane 1596 returns to its default flat shape, and the flow pattern returns to the original default configuration of FIG. 15(*a*).

Figure 16:
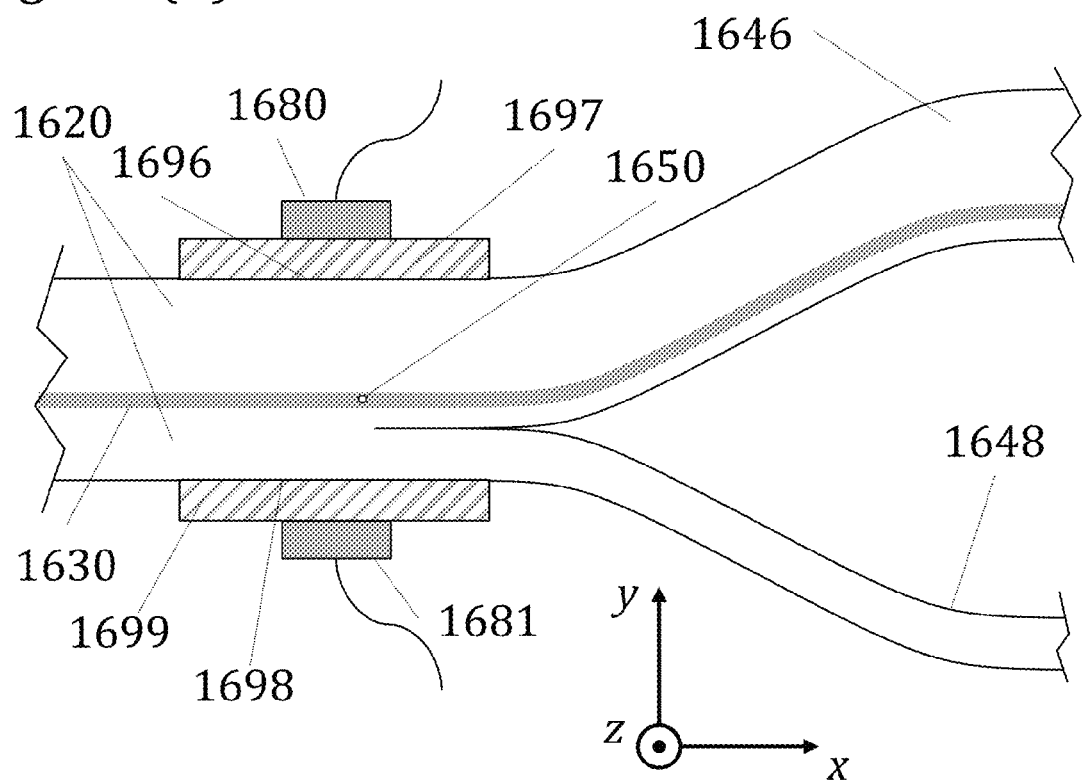
FIGS. 16(a) and (b) are schematic cross-sectional illustrations of two steps, or states, of a particle analysis/sorting method with two sorting states and two-sided actuation in accordance with one embodiment.
Figure 16:
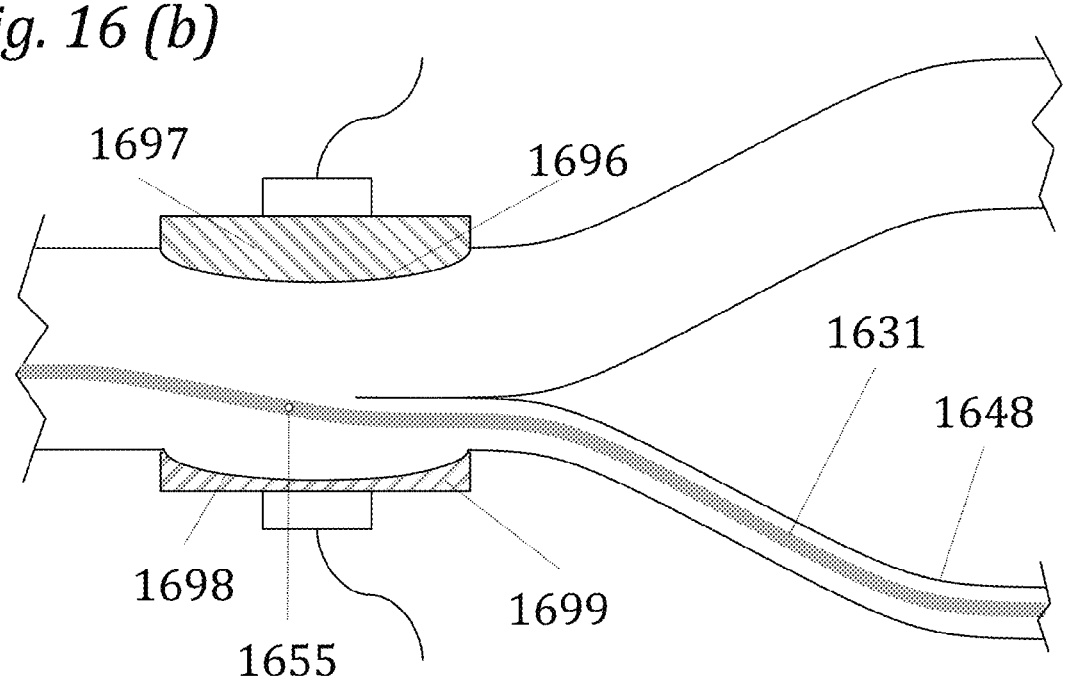

FIGS. 16(*a*) and 16(*b*) illustrate yet another embodiment of two states of a particle analysis and sorting method of the current invention. It is similar to the embodiment illustrated in FIGS. 15(*a*) and 15(*b*), except in the design of actuation. Sorting actuation here is realized by means of two actuators, positioned on opposite sides of the flowcell, each actuator being located in proximity to expandable/compressible chambers (1697 for the default side and 1699 for the sort side) adjacent to the flowcell inner wall and separated from the sheath fluid 1620 by a flexible membrane (1696 for the default side and 1698 for the sort side). In the default state, depicted in FIG. 16(*a*), the expandable chambers 1697 and 1699 of both the default-side and sort-side actuators are in their default configuration at pressures designed to match the pressure of the fluid inside the flowcell at the location of the membranes 1696 and 1698, resulting in flat shapes of the membranes to match the shape of the flowcell inner walls. In this non-sorting state, a non-selected particle 1650 in the sample core stream 1630 flows by design into the default sorting channel 1646. In the sorting state, depicted in FIG. 16(*b*), the expandable chamber 1697 of the default-side actuator 1680 is pressurized (by means including, for instance, heating means, mechanical means, hydraulic means, and gas injection means), through actuation, in a similar way as depicted in reference to FIG. 15(*b*); this pressure differential with respect to the local pressure in the sheath fluid causes the membrane 1696 to bulge into the flowcell until a new equilibrium is reached. Simultaneously, the compressible chamber 1699 of the sorting side actuator 1681 is depressurized (by means including, for instance, cooling means, mechanical means, hydraulic means, and gas aspiration means), through activation of actuator 1681, to a lower pressure than in the default configuration; this pressure differential with respect to the local pressure in the sheath fluid causes the membrane 1698 to flex away from the flowcell until a new equilibrium is reached. The combination of the inwardly bulging default-side membrane 1696 and the outwardly flexing sort-side membrane 1698 causes the flow pattern to shift in a similar way to that previously shown for FIGS. 14(*b*) and 15(*b*), resulting in the sample core stream 1631 being temporarily diverted into the sorting channel 1648, which sample stream contains a particle 1655 detected upstream and automatically selected by analysis algorithms to trigger sorting actuation. Following deactivation of the actuator pair, both the default-side and the sort-side expandable/compressible chambers 1697 and 1699 are allowed to or made to return to their default pressure states, both the default-side and the sort-side membranes 1696 and 1698 return to their default flat shapes, and the flow pattern returns to the original default configuration of FIG. 16(*a*).

Figure 17:
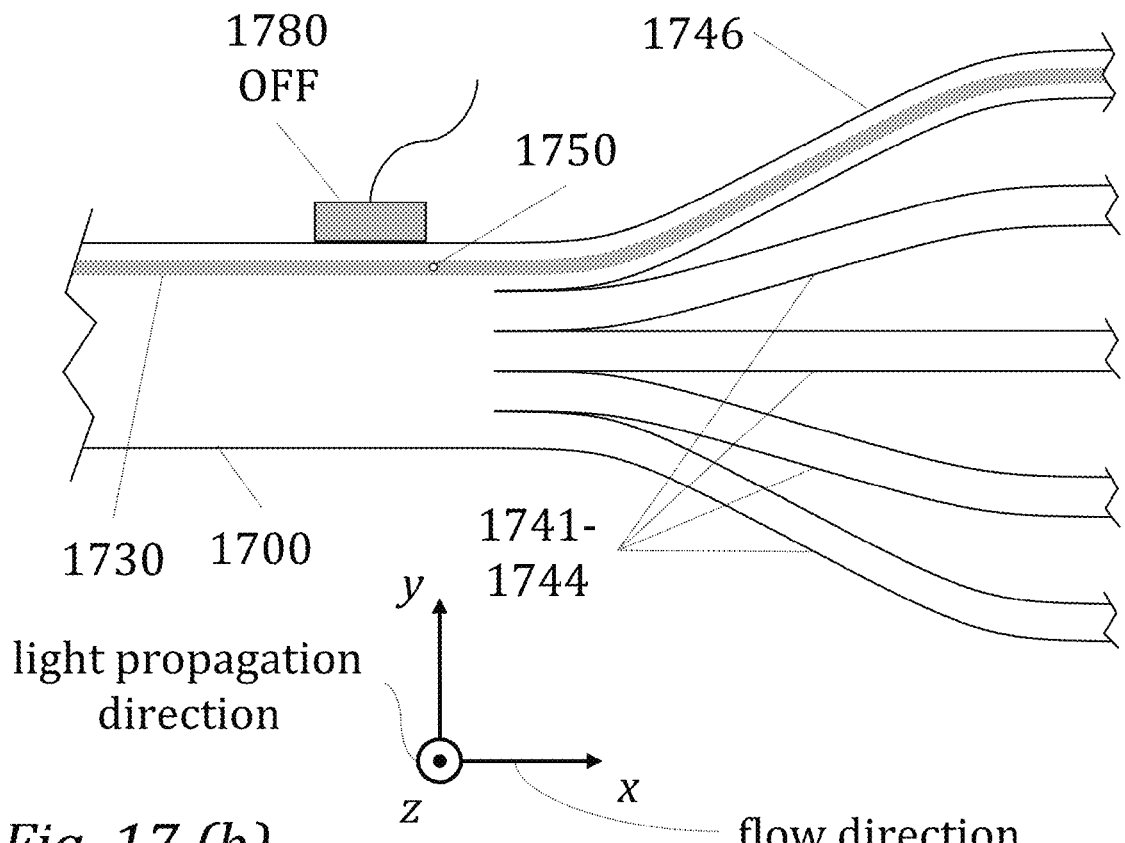
FIGS. 17(a)-(d) are schematic cross-sectional illustrations of four states of a particle analysis/sorting method with five sorting states and one-sided actuation that uses multiple sorting channels in accordance with one embodiment.
Figure 17:
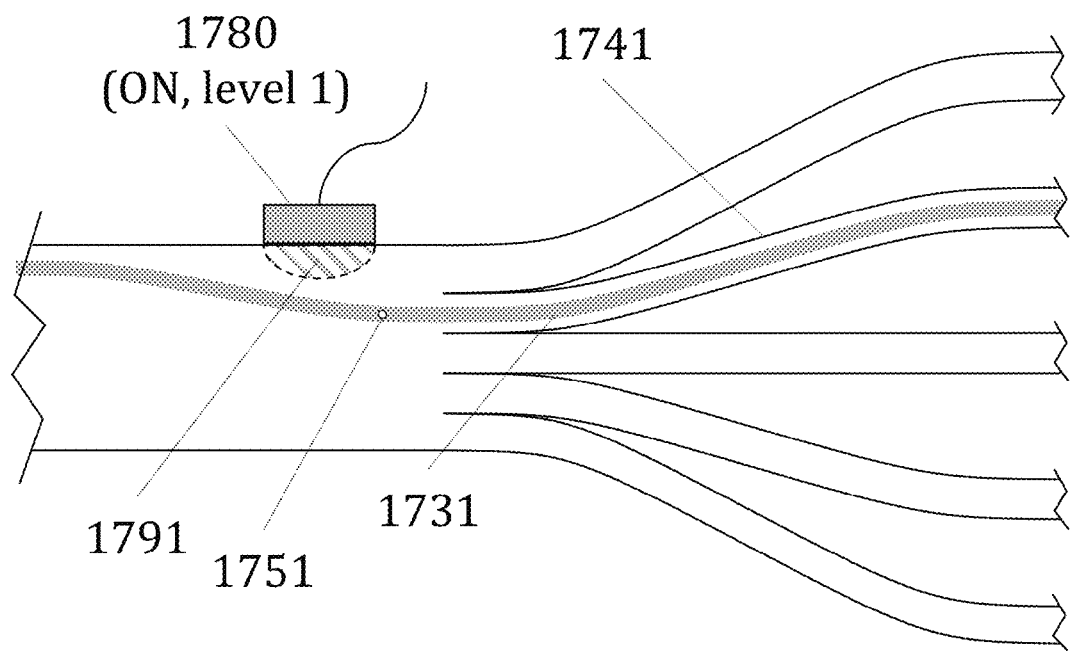
Figure 17:
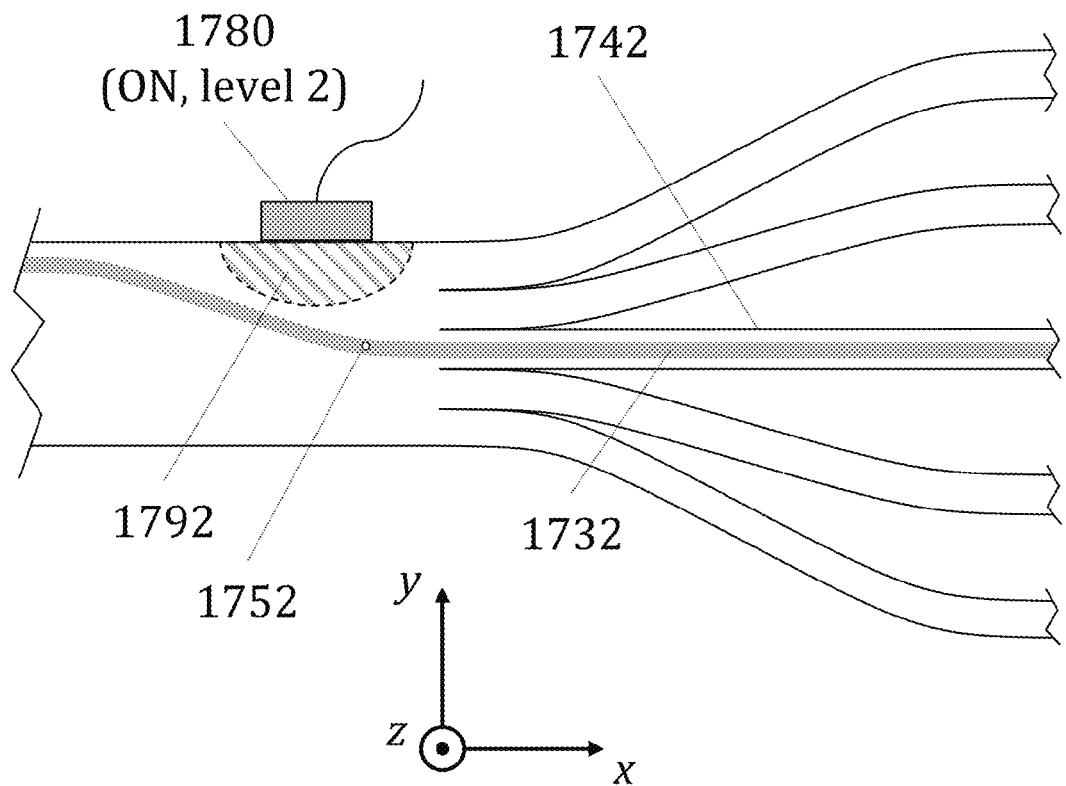
Figure 17:
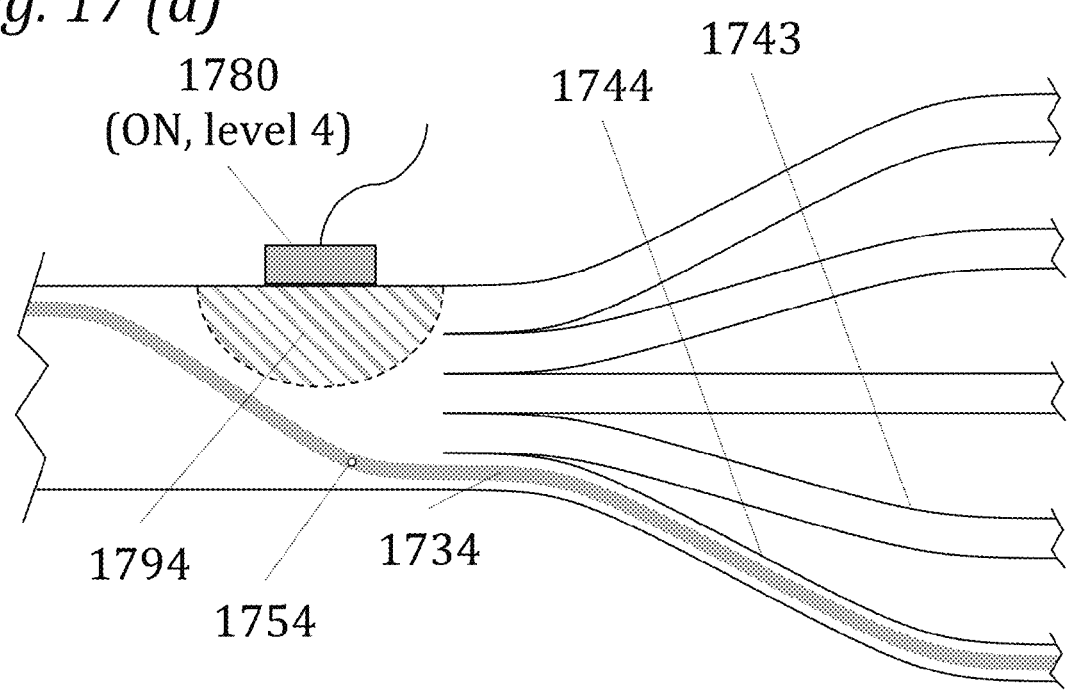

FIGS. 17(*a*)-(*d*) illustrate a multi-way sorting embodiment of a particle analysis and sorting method of the current invention. Each of the four figures shows a schematic representation of a cross-sectional view of the sorting region of the flowcell. The configuration is similar to that depicted in reference to FIGS. 14(*a*) and (*b*), except that instead of a single sorting channel, a plurality of sorting channels 1741-1744 is provided along a transverse direction y. One advantage of this embodiment is the ability to have a plurality of different receptacles into which the sample may be sorted, depending on the result of the upstream analysis by the interrogating light beam, the signal detectors, and associated electronic and logic trigger circuitry. For example, the signals detected in response to the upstream interrogation of the sample may indicate that a particle, e.g., particle 1751, was detected with a certain set A of properties targeted for selection (e.g., the presence of surface antigens or intracellular markers associated with certain kinds of cancer cells). It may be desirable to sort particles having these properties into a certain collection receptacle, e.g., one provided to receive the outflow from sorting channel 1741, as illustrated in FIG. 17(*b*). Another particle, e.g., particle 1752, may flow past the interrogation point and produce signals that indicate the presence of a different set B of properties targeted for selection (e.g., the presence of surface antigens or intracellular markers associated with certain kinds of stem cells). It would be desirable to sort particles like particle 1752 having set-B properties into a different receptacle from that designed for collection of particles having set-A properties: e.g., a receptacle provided to receive the outflow from sorting channel 1742, as illustrated in FIG. 17(*c*). Likewise for yet another set D of properties, particles like particle 1754 detected as having those properties, and a sorting channel 1744 designed to flow into a receptacle to collect such particles. Accordingly, the embodiment illustrated in FIGS. 17(*a*)-(*d*) provides an example of such a multi-way sorting capability of the current invention, with a number of sorting channels 1741-1744 in addition to the default sorting channel 1746. FIGS. 17(*a*)-(*d*) exemplarily show four such sorting channels explicitly. It will be apparent to those skilled in the art that additional configurations having more or less than four sorting channels, in addition to the default sorting channel, do not depart from the scope of the disclosed invention.

Each of the sorting channels 1741-1744 (as well as the default sorting channel 1746) may optionally be connected with a receiving receptacle designed to collect the fluid flow from the respective channel. The selection of a particular sorting channel (or of the default sorting channel) as the target for reception of a desired sorted portion of the sample core stream is effected by actuation of actuator 1780. In a two-way sort there are two principal sorting states, which can be described as OFF (default) and ON (sorting) as described above in relation to FIGS. 14(*a*)-(*b*), 15(*a*)-(*b*), and 16(*a*)-(*b*). In a multi-way sort, on the other hand, there generally can be as many sorting states as there are sorting "ways" or possible sorting channels. With reference to FIGS. 17(*a*)-(*d*), five possible sorting channels are indicated (the default sorting channel 1746 plus four sorting channels 1741-1744); accordingly, this is referred to as a five-way sort. An actuation process is provided to result in different degrees of deflection of the sample core stream portion, corresponding to the selection of different intended sorting channels.

In FIG. 17(*a*) actuator 1780 is depicted as embodied in, in contact with, or in proximity of the inner wall of the flowcell 1700 on the default sorting channel side. Similarly to the state depicted in FIG. 14(*a*), FIG. 17(*a*) shows the configuration of the default state, where with the actuator 1780 in the OFF state, a non-selected particle 1750 in the sample core stream 1730 flows by design into the default sorting channel 1746. Similarly to the state depicted in FIG. 14(*b*), FIGS. 17(*b*)-(*d*) show the configurations of various sorting states, where with the actuator 1780 in the ON state at levels 1, 2, and 4, respectively, transient regions 1791, 1792, and 1794, respectively (comprising, for instance, a gas, vapor, gas-vapor bubble, or a less-dense region of sheath fluid), are generated (by means including, for instance, thermal means, electrolytic means, and gas injection means), which create respective localized flow diversions in the depicted cross-sectional plane and in its vicinity, which diversions temporarily deflect the sample core stream into configurations 1731, 1732, and 1734, respectively, and cause the corresponding particles 1751, 1752, and 1754, respectively, to flow into the respective sorting channels 1741, 1742, and 1744. Following deactivation of the actuator, the transient gas bubble shrinks or is cleared away, and the flow pattern returns to the original default state of FIG. 17(*a*). Not shown is the configuration of a sorting state intermediate to the sorting states of FIGS. 17(*c*) and 17(*d*), corresponding to an actuation level 3, whereby a transient region of a size intermediate between that of regions 1792 and 1794 temporarily diverts the sample core stream into sorting channel 1743.

Throughout this disclosure the term "default sorting channel" is associated with an OFF state of an actuator, signifying a passive state in which no particle sorting is performed, and in which the sample core stream and particles therein are typically outflowed and discarded as undesired waste. The term "sorting channel" is associated with an ON state of an actuator, signifying an activated state of an actuator, in which active sorting of a desired particle is performed. While for some embodiments this may be a preferred configuration, the invention is not so limited, and included under the scope of the invention are embodiments where a passive state of an actuator is associated with collection of desired particles, and an active state of an actuator is associated with generation of a waste stream of undesired particles from the particle analyzer/sorter.

Figure 18:
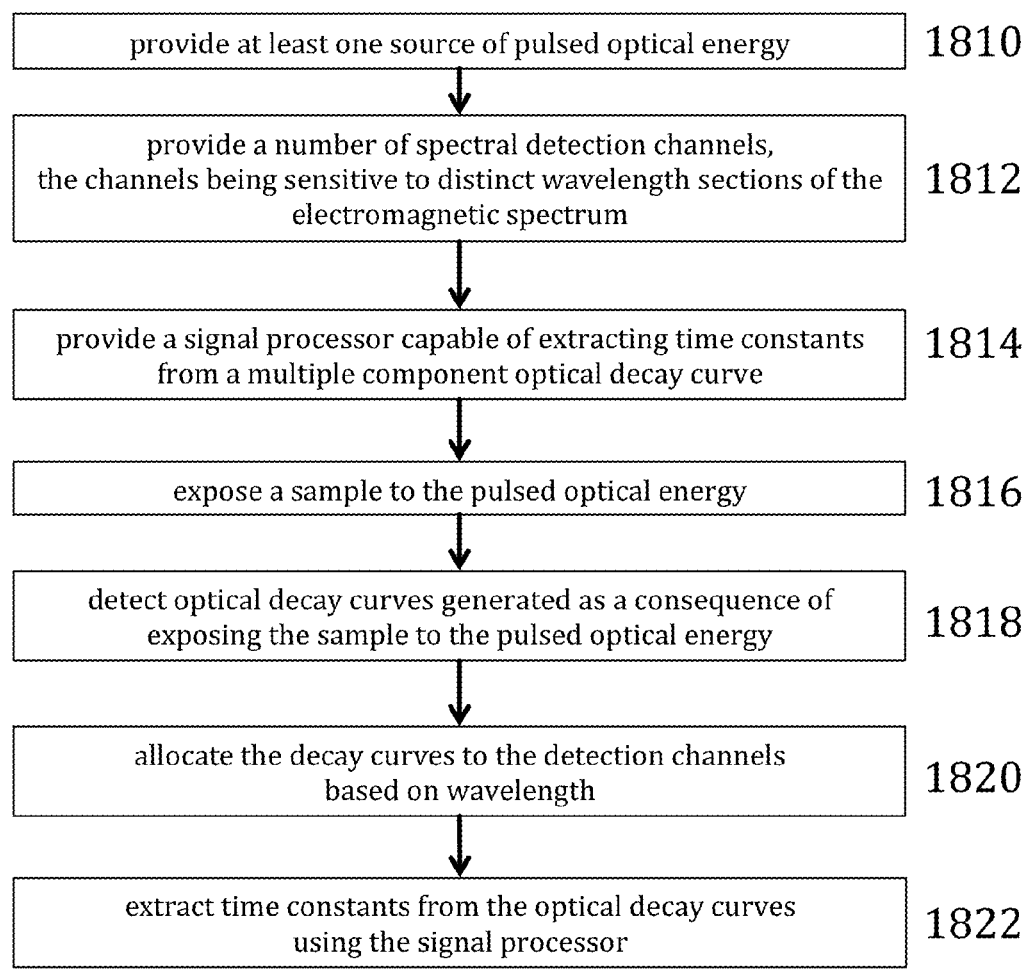
FIG. 18(a) is a flow chart describing a sequence of principal operations involved in the performance of a method of lifetime analysis in accordance with one embodiment.
FIG. 18(b) is a flow chart describing a sequence of principal operations involved in the performance of a method of particle analysis in accordance with one embodiment.
FIG. 18(c) is a flow chart describing a sequence of principal operations involved in the performance of a method of highly multiplexed particle analysis in accordance with one embodiment.
Figure 18:
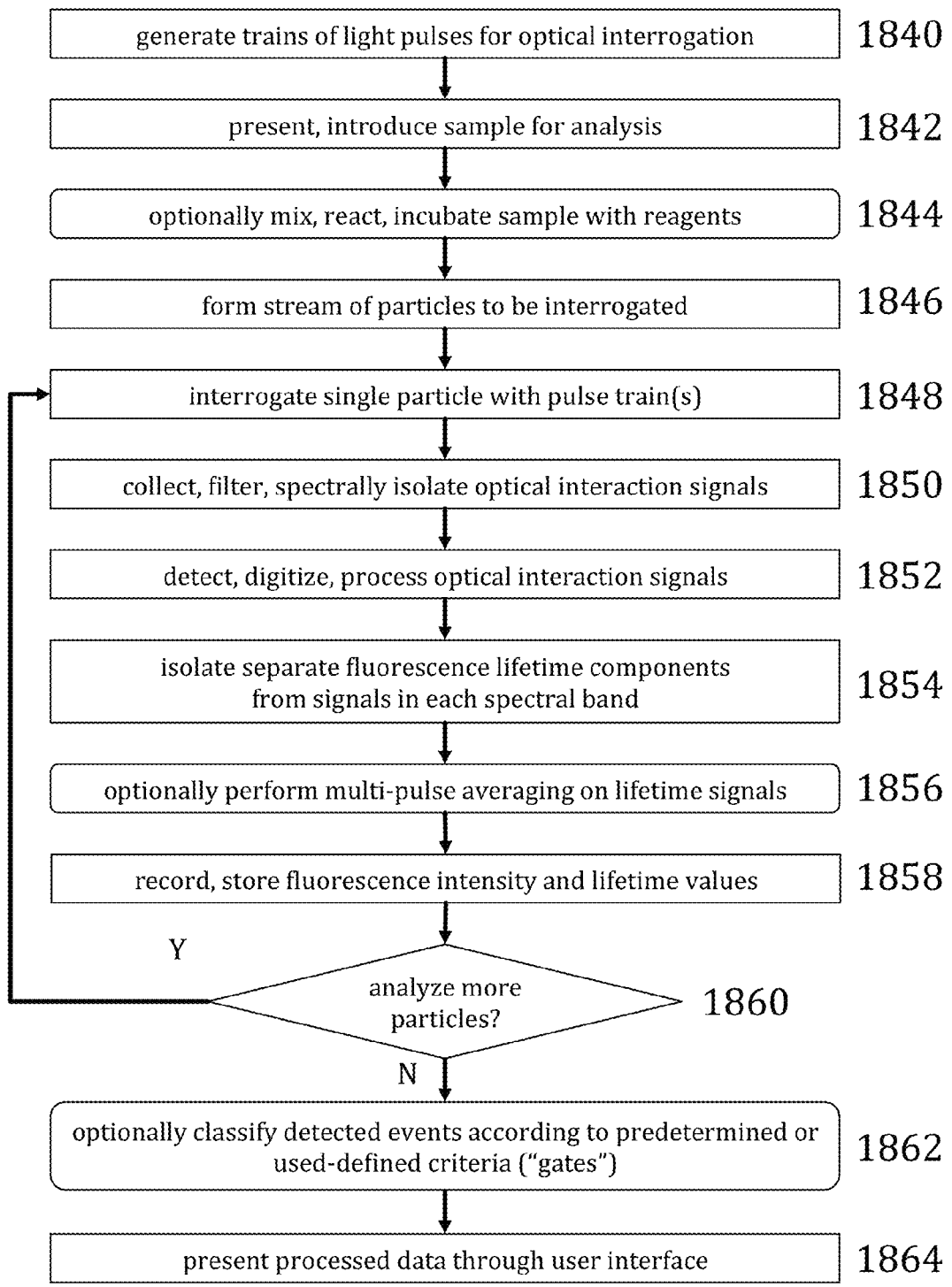
Figure 18:
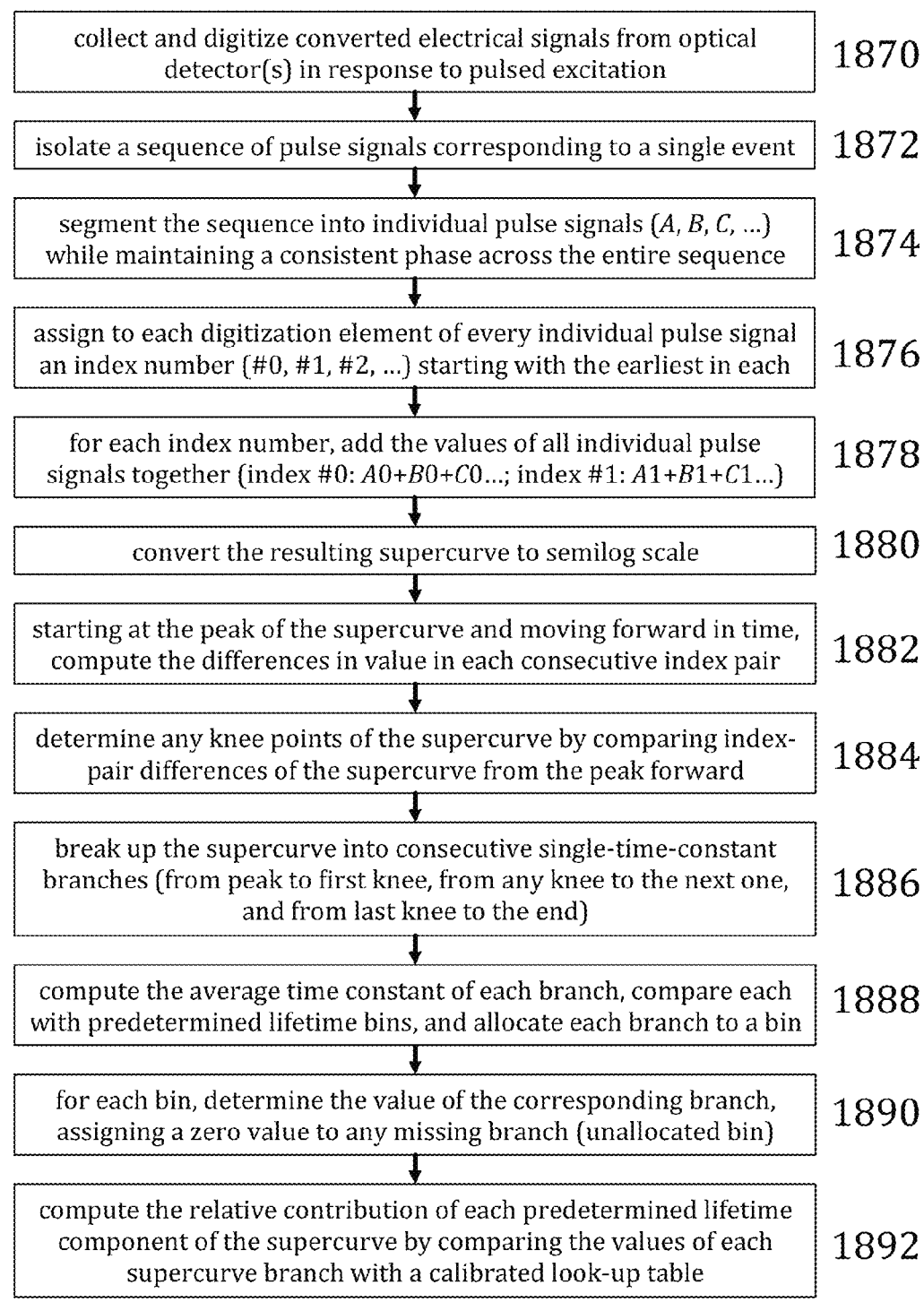

Referring to FIG. 18(*b*), a flow chart is provided that describes a sequence of principal steps involved in the performance of the step of particle analysis in accordance with an embodiment of the present invention. A first step 1840 involves the generation of one or more trains of optical pulses (or other modulated output of light from one or more sources) for optical interrogation of particles in a sample. A second step 1842 involves the presentation of a sample, or the introduction of a sample, to the apparatus by a user or operator. A third, optional, step 1844 involves the mixing, reaction, and incubation of the sample with one or more reagents, which reagents may be preloaded onboard the apparatus or may be introduced by the user or operator. A fourth step 1846 involves the formation, by means of hydrodynamic focusing of the sample by sheath fluid, of a core stream of particles flowing essentially in single file in the microchannel portion of the flowcell for optical interrogation. A fifth step 1848 involves the interrogation, by optical interaction, of a single particle in the sample core stream by the one or more trains of optical pulses, resulting in the generation of optical interaction signals. A sixth step 1850 involves the collection of the optical interaction signals, the optical filtering of the collected optical signals, and the spectral isolation of the filtered optical signals. A seventh step 1852 involves the detection of the spectrally isolated optical signals, the transduction of said signals into analog electrical signals, the digitization of the analog electrical signals into digital signals, and the processing of the digital signals. An eighth step 1854 involves the further application of digital signal processing algorithms to the digital signals corresponding to each isolated spectral band so as to isolate the separate contributions of one or more fluorescence lifetime components to each signal. A ninth optional step 1856 involves the averaging of lifetime signals coming from different pulses but all originating from the same particle under interrogation. A tenth step 1858 involves the recording and storage of the detected and processed signal parameters, such as, without limitation, fluorescence intensity in one or more spectral bands, one or more fluorescence lifetime values in each of the one or more spectral bands, phase shift, scattering intensity, and absorption. An eleventh step 1860 involves a decision, which may be automated or may be presented by the system, through a processing unit, to the user or operator as a call for action, on whether to analyze additional particles; if the choice is positive, the method workflow returns to the fifth step above; if the choice is negative, the method workflow continues to the next (twelfth) step below. A twelfth optional step 1862 involves the classification of a portion or a totality of the events detected and analyzed according to certain criteria (which may include, without limitation, entities commonly referred to in the art as "triggers," "thresholds," and "gates"), which may be predetermined and preloaded into the apparatus or may be selected or modified or created by the user. A thirteenth step 1864 involves the presentation to the user or operator of the processed data (which may include, without limitation, the raw detected time-varying signals, a list of detected particle-interrogation events, and graphs or plots of detected events displayed according to characteristics such as, e.g., fluorescence lifetime, fluorescence intensity, and scattering) by means of a user interface such as, e.g., a screen, a computer monitor, a printout, or other such means.

Figure 19:
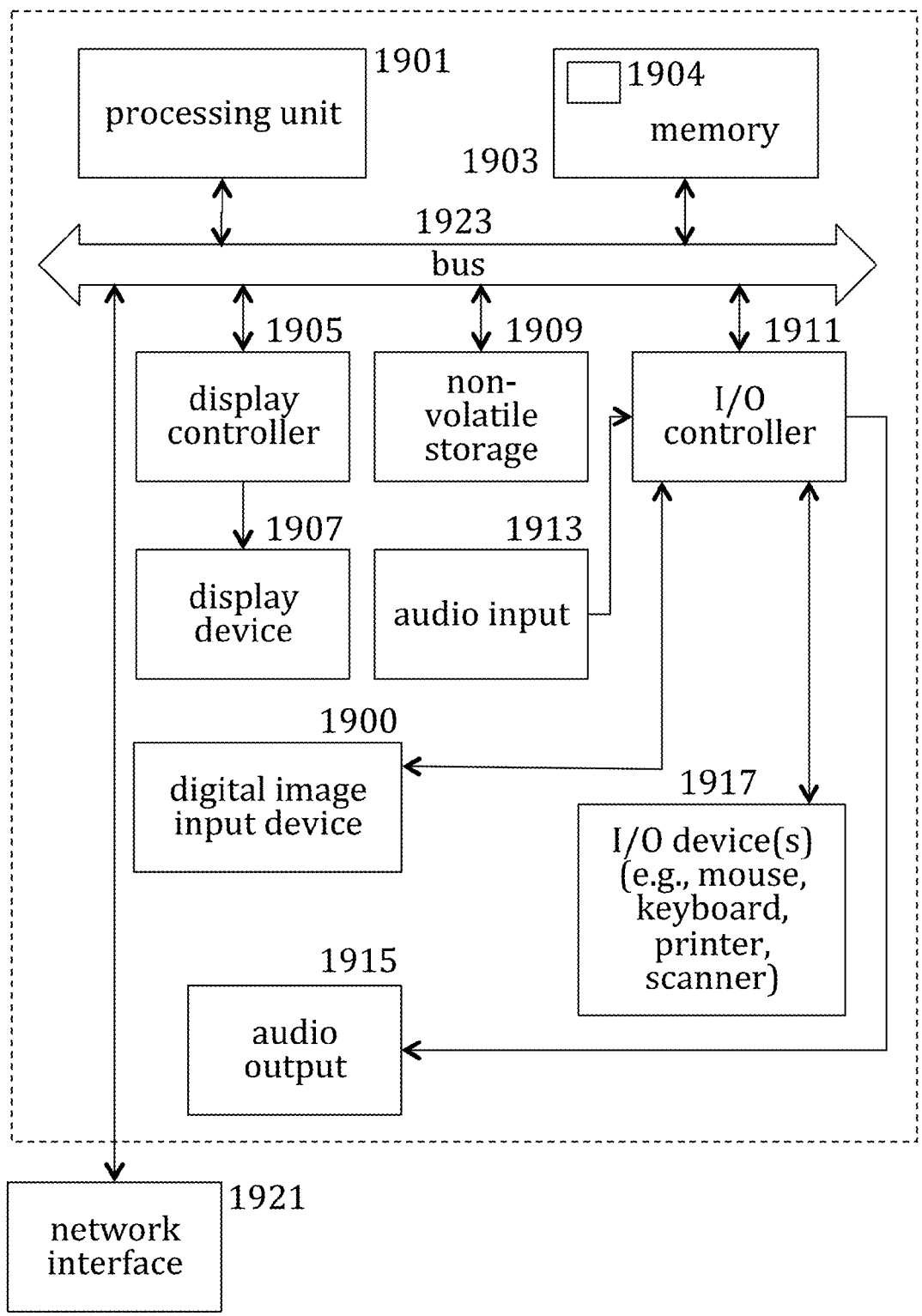
FIG. 19 is a schematic representation of a data processing system to provide an analyzer/sorter in accordance with one embodiment.

FIG. 19 shows a block diagram of an exemplary embodiment of a data processing system 1900 to provide a particle analysis and sorting system as described herein. In an embodiment, data processing system 1900 is a part of the control system to perform a method that includes providing light pulses; providing a sample for analysis; exposing the sample to the light pulses; detecting optical decay curves;

and extracting time constants from the optical decay curves, as described herein. In some embodiments, data processing system 1900 is represented by any one of signal processing units 790, 890, 990 and 1090 depicted in FIGS. 7, 8, 9, and 10, respectively, and further optionally incorporates any one of data storage units 792 and 892 depicted in FIGS. 7 and 8, respectively.

Data processing system 1900 includes a processing unit 1901 that may include a microprocessor or microcontroller, such as Intel microprocessor (e.g., Core i7, Core 2 Duo, Core 2 Quad, Atom), Sun Microsystems microprocessor (e.g., SPARC), IBM microprocessor (e.g., IBM 750), Motorola microprocessor (e.g., Motorola 68000), Advanced Micro Devices ("AMD") microprocessor, Texas Instrument microcontroller, and any other microprocessor or microcontroller.

Processing unit 1901 may include a personal computer (PC), such as a Macintosh® (from Apple Inc. of Cupertino, Calif.), Windows®-based PC (from Microsoft Corporation of Redmond, Wash.), or one of a wide variety of hardware platforms that run the UNIX operating system or other operating systems. For at least some embodiments, processing unit 1901 includes a general purpose or specific purpose data processing system based on Intel, AMD, Motorola, IBM, Sun Microsystems, IBM processor families, or any other processor families. As shown in FIG. 19, a memory 1903 is coupled to the processing unit 1901 by a bus 1923. Memory 1903 has instructions and data 1904 stored thereon which when accessed by processing unit 1901 cause the processing unit 1901 to perform methods to provide highly multiplexed particle analysis or lifetime analysis, and optionally sorting, as described herein.

Memory 1903 can be dynamic random access memory ("DRAM") and can also include static random access memory ("SRAM"). A bus 1923 couples processing unit 1901 to memory 1903 and also to a non-volatile storage 1909 and to a display controller 1905 (if a display is used) and to input/output (I/O) controller(s) 1911. Display controller 1905 controls in the conventional manner a display on a display device 1907 which can be a cathode ray tube (CRT), a liquid crystal display (LCD), a light-emitting diode (LED) monitor, a plasma monitor, or any other display device. Input/output devices 1917 can include a keyboard, disk drives, printers, a scanner, a camera, and other input and output devices, including a mouse or other pointing device. I/O controller 1911 is coupled to one or more audio input devices 1913 such as, for example, one or more microphones.

Display controller 1905 and I/O controller 1911 can be implemented with conventional well-known technology. An audio output 1915 such as, for example, one or more speakers, may be coupled to I/O controller 1911. Non-volatile storage 1909 is often a magnetic hard disk, an optical disk, or another form of storage for large amounts of data. Some of this data is often written, by a direct memory access process, into memory 1903 during execution of software in data processing system 1900 to perform methods described herein.

One of skilled in the art will immediately recognize that the terms "computer-readable medium" and "machine-readable medium" include any type of storage device that is accessible by processing unit 1901. Data processing system 1900 can interface to external systems through a modem or network interface 1921. It will be appreciated that modem or network interface 1921 can be considered to be part of data processing system 1900. This interface 1921 can be an analog modem, ISDN modem, cable modem, token ring interface, satellite transmission interface, Wi-Fi, Bluetooth, cellular network communication interface, or other interfaces for coupling a data processing system to other data processing systems.

It will be appreciated that data processing system 1900 is one example of many possible data processing systems which have different architectures. For example, personal computers based on an Intel microprocessor often have multiple buses, one of which can be an input/output (I/O) bus for the peripherals and one that directly connects processing unit 1901 and memory 1903 (often referred to as a memory bus). The buses are connected together through bridge components that perform any necessary translation due to differing bus protocols.

Network computers are another type of data processing system that can be used with the embodiments as described herein. Network computers do not usually include a hard disk or other mass storage, and the executable programs are loaded from a network connection into memory 1903 for execution by processing unit 1901. A typical data processing system will usually include at least a processor, memory, and a bus coupling the memory to the processor.

It will also be appreciated that data processing system 1900 can be controlled by operating system software which includes a file management system, such as a disk operating system, which is part of the operating system software. Operating system software can be the family of operating systems known as Macintosh® Operating System (Mac OS®) or Mac OS X® from Apple Inc. of Cupertino, Calif., or the family of operating systems known as Windows® from Microsoft Corporation of Redmond, Wash., and their associated file management systems. The file management system is typically stored in non-volatile storage 1909 and causes processing unit 1901 to execute the various acts required by the operating system to input and output data and to store data in memory, including storing files on non-volatile storage 1909.

In various embodiments, hardwired circuitry may be used in combination with software instructions to implement methods described herein. A non-transitory machine-readable medium can be used to store software and data which when executed by a data processing system causes the system to perform various methods described herein. This executable software and data may be stored in various places including for example ROM, volatile RAM, non-volatile memory, and/or cache. Portions of this software and/or data may be stored in any one of these storage devices.

Thus, a machine-readable medium includes any mechanism that provides (i.e., stores and/or transmits) information in a form accessible by a machine (e.g., a computer, network device, or any device with a set of one or more processors, etc.). For example, a machine-readable medium includes recordable/non-recordable media (e.g., read only memory (ROM); random access memory (RAM); magnetic disk storage media; optical storage media; flash memory devices; and the like).

It will be further appreciated that data processing system 1900 may be functionally implemented by allocating several of its functions to distributed units or modules separate from a central system. In some embodiments, some or all of the signal processing functions as depicted, e.g., in FIGS. 7-10, illustrated in FIGS. 11(*a*)-(*f*) and 12(*a*)-(*b*), and described in FIGS. 18(*a*)-(*c*), may be performed by signal processing units or modules physically separate from data processing system 1900, yet connected with it for performance of other functions, such as, e.g., input/output, display, data storage, memory usage, bus usage, additional signal processing functions, and both specific-purpose and general-purpose data processing functions. In some embodiments, some or all of the data storage functions as depicted, e.g., in FIGS. 7-8, illustrated in FIGS. 11(a)-(f) and 12(a)-(b), and described in FIGS. 18(a)-(c), may be performed by data storage units or modules physically separate from data processing system 1900, yet connected with it as described above. In some embodiments, some or all of the signal processing functions mentioned may be performed by processing unit 1901 internal to data processing system 1900, and in some embodiments some or all of the data storage functions mentioned may be performed by non-volatile storage unit 1909 and/or memory unit 1903 internal to data processing system 1900.

The methods as described herein can be implemented using dedicated hardware (e.g., using Field Programmable Gate Arrays, Digital Signal Processing chips, or Application Specific Integrated Circuits) or shared circuitry (e.g., microprocessors, microcontrollers, single-board computers, stand-alone computers, or cloud-based processors on remote servers) under control of program instructions stored in a machine-readable medium. The methods as described herein can also be implemented as computer instructions for execution on a data processing system, such as system 1900 of FIG. 19.

It will be appreciated by those skilled in the art that aspects of the present invention, while illustrated with reference to applications to particle analysis and sorting and particularly to flow cytometry, also present advantages in other application areas. The concept of lifetime binning as a means to simplify the performance of lifetime measurements and thereby enable higher degree of multiplexing than hitherto practical, for example, is also advantageous to the field of imaging, in particular to the field of microscopy, and more particularly to the field of fluorescence microscopy. Whereas in a flow cytometer an "event" is defined as the passage of a particle through the interrogation area, in microscopy the roughly equivalent element is a "pixel," defined as the smallest resolvable unit of an image. Spectral spillover and crosstalk is a problem in fluorescence microscopy just as it is a problem in flow cytometry, and the present invention offers a solution to both by providing a greater degree of multiplexing, a reduced level of spectral spillover, or a combination of the two. The present invention admits of implementation within the framework of a fluorescence microscope in ways that parallel very closely the specific examples given in the case of flow-based particle analysis. A microscopy application of the present invention, for example, would rely on a system configuration very similar to that of FIG. 7, with the fluid elements 740, 742, 700, and 740 replaced by a suitable sample holder, such as are well known in the art, for exposure of the sample to the beam; and similarly for FIGS. 9 and 10. In other words, adaptation of the present invention to the field of microscopy is fully within the scope of this disclosure, given the descriptions of the novel apparatus and methods herein. One specific application of fluorescence microscopy that would benefit from the present invention is in vivo imaging, such as, e.g., methods and apparatuses used for medical diagnostics. These include the analysis and diagnosis of externally optically accessible organs, such as the skin and the eye, as well as organs optically accessible through the use of endoscopes, such as the respiratory tract, the gastrointestinal tract, and, in the context of surgery, any other organ or part of the body. As in the case of laboratory-based fluorescence microscopy, adaptation of the apparatuses and methods described herein is entirely within the scope of the present invention, requiring only minor modifications of the apparatus and process steps from the illustrative examples that are provided. The usefulness of the present invention is therefore not to be circumscribed to the examples and figures provided, but extends to the full scope of what is claimed.

A method of analyzing particles in a sample using a particle analyzer is disclosed, comprising the steps of:
  providing a source of a beam of pulsed optical energy;
  providing a sample holder configured to expose a sample to the beam;
  providing a detector, the detector comprising a number of spectral detection channels, the channels being sensitive to distinct wavelength sections of the electromagnetic spectrum and being configured to detect optical signals resulting from interactions between the beam and the sample, the channels being further configured to convert the optical signals into respective electrical signals;
  providing a first optical path from the source of the beam to the sample;
  providing a second optical path from the sample to the detector;
  providing a signal processing module;
  exposing the sample to the beam, and
  using the signal processing module for:
  receiving the electrical signals from the detector;
  mathematically combining individual decay curves in the electrical signals into a decay supercurve, said supercurve comprising a number of components, each component having a time constant and a relative contribution to the supercurve;
  extracting time constants from the supercurve; and
  quantifying the relative contribution of individual components to the supercurve.

A method of analyzing and sorting particles in a sample using a particle analyzer/sorter is disclosed, comprising the steps of:
  providing an internally modulated laser as a source of a beam of pulsed optical energy;
  providing a flowcell configured as an optical excitation chamber for exposing to the beam a sample comprising a suspension of particles and for generating optical signals from interactions between the beam and the particles;
  providing a detector, the detector comprising a number of spectral detection channels, the channels being sensitive to distinct wavelength sections of the electromagnetic spectrum and being configured to detect fluorescence optical signals resulting from interactions between the beam and the particles in the sample, the channels being further configured to convert the optical signals into respective electrical signals;
  providing a first optical path from the source of the beam to the sample;
  providing a second optical path from the sample to the detector;
  providing a flow path for the suspension of particles;
  providing connections between the flowcell and each of the flow path, the first optical path, and the second optical path;
  providing a signal processing module comprising one of an FPGA, a DSP chip, an ASIC, a CPU, a microprocessor, a microcontroller, a single-board computer, a standalone computer, and a cloud-based processor;
  exposing the particles in the sample to the beam;
  using the signal processing module for:

receiving the electrical signals from the detector;
mathematically combining individual decay curves in the electrical signals into a decay supercurve, said supercurve comprising a number of components, each component having a time constant and a relative contribution to the supercurve;
extracting time constants from the supercurve; and
quantifying the relative contribution of individual components to the supercurve;
providing a particle sorting actuator connected with the flow path, based on at least one flow diversion in the flow path, and further based on one of a transient bubble, a pressurizable chamber, a pressurizable/depressurizable chamber pair, and a pressure transducer;
providing an actuator driver connected with the actuator, the driver being configured to receive actuation signals from the signal processing module;
providing at least one particle collection receptacle; and
collecting at least one particle from the suspension of particles in the particle collection receptacle.

A method of analyzing particles in a sample using a particle analyzer is disclosed, comprising the steps of:
providing a source of a beam of pulsed optical energy;
providing a sample holder configured to expose a sample to the beam;
providing a detector, the detector comprising a number of spectral detection channels, the channels being sensitive to distinct wavelength sections of the electromagnetic spectrum and being configured to detect optical signals resulting from interactions between the beam and the sample, the channels being further configured to convert the optical signals into respective electrical signals;
providing a first optical path from the source of the beam to the sample;
providing a second optical path from the sample to the detector;
providing a signal processing module;
exposing the sample to the beam, and
using the signal processing module for:
receiving the electrical signals from the detector;
mathematically combining individual decay curves in the electrical signals into a decay supercurve, said supercurve comprising a number of components, each component having a time constant and a relative contribution to the supercurve;
allocating individual components of the supercurve to discrete bins of predetermined time constants; and
quantifying the relative contribution of individual components to the supercurve.

A method of analyzing and sorting particles in a sample using a particle analyzer/sorter is disclosed, comprising the steps of:
providing an internally modulated laser as a source of a beam of pulsed optical energy;
providing a flowcell configured as an optical excitation chamber for exposing to the beam a sample comprising a suspension of particles and for generating optical signals from interactions between the beam and the particles;
providing a detector, the detector comprising a number of spectral detection channels, the channels being sensitive to distinct wavelength sections of the electromagnetic spectrum and being configured to detect fluorescence optical signals resulting from interactions between the beam and the particles in the sample, the channels being further configured to convert the optical signals into respective electrical signals;
providing a first optical path from the source of the beam to the sample;
providing a second optical path from the sample to the detector;
providing a flow path for the suspension of particles;
providing connections between the flowcell and each of the flow path, the first optical path, and the second optical path;
providing a signal processing module comprising one of an FPGA, a DSP chip, an ASIC, a CPU, a microprocessor, a microcontroller, a single-board computer, a standalone computer, and a cloud-based processor;
exposing the particles in the sample to the beam;
using the signal processing module for:
receiving the electrical signals from the detector;
mathematically combining individual decay curves in the electrical signals into a decay supercurve, said supercurve comprising a number of components, each component having a time constant and a relative contribution to the supercurve;
allocating individual components of the supercurve to discrete bins of predetermined time constants; and
quantifying the relative contribution of individual components to the supercurve;
providing a particle sorting actuator connected with the flow path, based on at least one flow diversion in the flow path, and further based on one of a transient bubble, a pressurizable chamber, a pressurizable/depressurizable chamber pair, and a pressure transducer;
providing an actuator driver connected with the actuator, the driver being configured to receive actuation signals from the signal processing module;
providing at least one particle collection receptacle; and
collecting at least one particle from the suspension of particles in the particle collection receptacle.

In the foregoing specification, embodiments of the invention have been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. An apparatus for analyzing an optical signal decay, comprising:
a source of a beam of pulsed optical energy;
a sample holder configured to expose a sample to said beam;
a detector, the detector comprising a number of spectral detection channels, said channels being sensitive to distinct wavelength sections of the electromagnetic spectrum and being configured to detect optical signals resulting from interactions between said beam and said sample, said channels being further configured to convert said optical signals into respective electrical signals;
a first optical path from said source of said beam to said sample;
a second optical path from said sample to said detector; and
a signal processing module, capable of:
receiving said electrical signals from said detector;
mathematically combining individual decay curves in said electrical signals into a decay supercurve, said supercurve comprising a number of components, each component having a time constant and a relative contribution to said supercurve;

extracting time constants from said supercurve; and quantifying the relative contribution of individual components to said supercurve.

2. The apparatus of claim 1, wherein
said source of said beam of pulsed optical energy is an internally modulated laser.

3. The apparatus of claim 1, wherein
said signal processing module comprises one of an FPGA, a DSP chip, an ASIC, a CPU, a microprocessor, a microcontroller, a single-board computer, a standalone computer, and a cloud-based processor.

4. The apparatus of claim 1, wherein said optical signals comprise a fluorescence signal.

5. The apparatus of claim 1, wherein said sample comprises a suspension of particles; the apparatus further comprising:
a flow path for said suspension of particles;
a flowcell configured as an optical excitation chamber for generating said optical signals from interactions between said beam of pulsed optical energy and said particles;
said flowcell being connected with said flow path, said first optical path and said second optical path.

6. The apparatus of claim 5, wherein the apparatus comprises a flow cytometer.

7. The apparatus of claim 6, further comprising:
a particle sorting actuator connected with said flow path;
an actuator driver connected with said actuator, said driver being configured to receive actuation signals from said signal processing module; and
at least one particle collection receptacle connected with said flow path.

8. The apparatus of claim 7, wherein
said particle sorting actuator is based on at least one flow diversion in said flow path.

9. The apparatus of claim 8, wherein
said particle sorting actuator is based on one of a transient bubble, a pressurizable chamber, a pressurizable/depressurizable chamber pair, and a pressure transducer.

10. An apparatus for analyzing an optical signal decay, comprising:
a source of a beam of pulsed optical energy;
a sample holder configured to expose a sample to said beam;
a detector, the detector comprising a number of spectral detection channels, said channels being sensitive to distinct wavelength sections of the electromagnetic spectrum and being configured to detect optical signals resulting from interactions between said beam and said sample, said channels being further configured to convert said optical signals into respective electrical signals;
a first optical path from said source of said beam to said sample;
a second optical path from said sample to said detector; and
a signal processing module, capable of:
receiving said electrical signals from said detector;
mathematically combining individual decay curves in said electrical signals into a decay supercurve, said supercurve comprising a number of components, each component having a time constant and a relative contribution to said supercurve;
allocating individual components of said supercurve to discrete bins of predetermined time constants; and
quantifying the relative contribution of individual components to said supercurve.

11. The apparatus of claim 10, wherein
said source of said beam of pulsed optical energy is an internally modulated laser.

12. The apparatus of claim 10, wherein
said signal processing module comprises one of an FPGA, a DSP chip, an ASIC, a CPU, a microprocessor, a microcontroller, a single-board computer, a standalone computer, and a cloud-based processor.

13. The apparatus of claim 10, wherein said optical signals comprise a fluorescence signal.

14. The apparatus of claim 10, wherein said sample comprises a suspension of particles; the apparatus further comprising:
a flow path for said suspension of particles;
a flowcell configured as an optical excitation chamber for generating said optical signals from interactions between said beam of pulsed optical energy and said particles;
said flowcell being connected with said flow path, said first optical path and said second optical path.

15. The apparatus of claim 14, wherein the apparatus comprises a flow cytometer.

16. The apparatus of claim 15, further comprising:
a particle sorting actuator connected with said flow path;
an actuator driver connected with said actuator, said driver being configured to receive actuation signals from said signal processing module; and
at least one particle collection receptacle connected with said flow path.

17. The apparatus of claim 16, wherein
said particle sorting actuator is based on at least one flow diversion in said flow path.

18. The apparatus of claim 17, wherein
said particle sorting actuator is based on one of a transient bubble, a pressurizable chamber, a pressurizable/depressurizable chamber pair, and a pressure transducer.

* * * * *